US012156760B2

(12) United States Patent
Camps et al.

(10) Patent No.: US 12,156,760 B2
(45) Date of Patent: Dec. 3, 2024

(54) CARDIAC PHASE GATING SYSTEM FOR RADIATION THERAPY

(71) Applicant: EBAMED SA, Geneva (CH)

(72) Inventors: Saskia Camps, Prangins (CH);
Adriano Garonna, Geneva (CH);
Jeremie Gringet, Lausanne (CH)

(73) Assignee: EBAMed SA, Geneva (CH)

( * ) Notice: Subject to any disclaimer, the term of this patent is extended or adjusted under 35 U.S.C. 154(b) by 258 days.

(21) Appl. No.: 17/776,004

(22) PCT Filed: Nov. 11, 2020

(86) PCT No.: PCT/IB2020/000930
§ 371 (c)(1),
(2) Date: May 11, 2022

(87) PCT Pub. No.: WO2021/094824
PCT Pub. Date: May 20, 2021

(65) Prior Publication Data
US 2022/0386987 A1 Dec. 8, 2022

Related U.S. Application Data

(60) Provisional application No. 62/935,279, filed on Nov. 14, 2019, provisional application No. 63/028,053, filed on May 21, 2020.

(51) Int. Cl.
*A61B 6/00* (2024.01)
*A61B 5/00* (2006.01)
(Continued)

(52) U.S. Cl.
CPC .......... *A61B 8/0883* (2013.01); *A61B 5/7289* (2013.01); *A61B 6/541* (2013.01)

(58) Field of Classification Search
CPC ............................ A61N 5/1068; A61N 5/1049
See application file for complete search history.

(56) References Cited

U.S. PATENT DOCUMENTS 3,399,302 A   8/1968   Carrell
3,923,060 A   12/1975  Ellinwood, Jr.
(Continued)

FOREIGN PATENT DOCUMENTS

BE   1024702 A1   5/2018
CA   2781536 A1   12/2012
(Continued)

OTHER PUBLICATIONS

Klein et al., "Task Group 142 Report: Quality Assuance of Medical Accelerators," Medical Physsics, vol. 36, No. 9, pp. 4197-4212, Sep. 2009.
(Continued)

*Primary Examiner* — Dani Fox
(74) *Attorney, Agent, or Firm* — Greenberg Traurig, LLP; Christopher C. Bolten; Robert D. Ward

(57) ABSTRACT

Systems and techniques for reliably predicting a motion phase for non-invasive treatment of the heart. The system and methods may account for both respiratory and cardiac cycles in characterizing the motion of the heart relative to the irradiation source. The system and methods may also include a heartbeat sensor that provides an independent reference indication of the cardiac phase to provide real-time or near real-time quality assurance of a current predicted phase indication. The disclosed system and methods may be configured for use in one of two modes: "beam-gating" and "beam-tracking". For beam-gating, the predicted cardiac phase is compared to the desired gating window, based on the patient-specific treatment plan, to determine if a gate ON or gate OFF signal should be set. For beam-tracking, the predicted cardiac phase is used to load the appropriate beam
(Continued)

parameters based on the patient-specific and motion phase-dependent treatment plans.

32 Claims, 9 Drawing Sheets

(51) Int. Cl.
  *A61B 8/08* (2006.01)
  *A61N 5/00* (2006.01)

(56) References Cited

U.S. PATENT DOCUMENTS

| | | | |
|---|---|---|---|
| 5,538,494 A | 7/1996 | Matsuda | |
| 5,590,657 A | 1/1997 | Cain et al. | |
| 5,718,241 A | 2/1998 | Ben-Haim et al. | |
| 5,764,723 A | 6/1998 | Weinberger et al. | |
| 5,909,476 A | 6/1999 | Cheng et al. | |
| 6,144,875 A | 11/2000 | Schweikard et al. | |
| 6,443,896 B1 | 9/2002 | Detmer | |
| 6,658,285 B2 | 12/2003 | Potse et al. | |
| 6,710,362 B2 | 3/2004 | Kraft et al. | |
| 6,780,152 B2 | 8/2004 | Üstüner et al. | |
| 6,863,653 B1 | 3/2005 | Zanelli et al. | |
| 6,889,695 B2 | 5/2005 | Pankratov et al. | |
| 7,260,426 B2 | 8/2007 | Schweikard et al. | |
| 7,322,929 B2 | 1/2008 | Lovoi | |
| 7,346,381 B2 | 3/2008 | Okerlund et al. | |
| 7,565,190 B2 | 7/2009 | Okerlund et al. | |
| 7,645,276 B2 | 1/2010 | Pankratov et al. | |
| 7,853,313 B2 | 12/2010 | Thomson | |
| 7,953,204 B2 | 5/2011 | Sumanaweera et al. | |
| 8,278,633 B2 | 10/2012 | Nord et al. | |
| 8,295,435 B2 | 10/2012 | Wang et al. | |
| 8,295,906 B2 | 10/2012 | Saunders et al. | |
| 8,348,846 B2 | 1/2013 | Günther et al. | |
| 8,351,571 B2 | 1/2013 | Brinks et al. | |
| 8,422,631 B2 | 4/2013 | Takahashi et al. | |
| 8,488,910 B2 | 7/2013 | Ruijters | |
| 8,784,290 B2 | 7/2014 | Sumanaweera et al. | |
| 8,792,613 B2 | 7/2014 | Gardner et al. | |
| 8,805,481 B2 | 8/2014 | Sumanaweera et al. | |
| 8,824,757 B2 | 9/2014 | Kolthammer et al. | |
| 9,014,424 B2 | 4/2015 | Berlinger et al. | |
| 9,061,144 B2 | 6/2015 | Fujii et al. | |
| 9,108,048 B2 | 8/2015 | Maurer, Jr. et al. | |
| 9,205,279 B2 | 12/2015 | Sumanaweera et al. | |
| 9,289,268 B2 | 3/2016 | Ramraj et al. | |
| 9,320,916 B2 | 4/2016 | Sumanaweera et al. | |
| 9,326,751 B2 | 5/2016 | Hastings | |
| 9,504,853 B2 | 11/2016 | Sumanaweera et al. | |
| 9,526,476 B2 | 12/2016 | Schwartz et al. | |
| 9,750,957 B2 | 9/2017 | Fujii et al. | |
| 9,789,339 B2 | 10/2017 | Moskvin et al. | |
| 9,907,978 B2 | 3/2018 | Pankratov et al. | |
| 9,962,562 B2 | 5/2018 | Fahrig et al. | |
| 9,968,801 B2 | 5/2018 | Sumanaweera et al. | |
| 10,029,121 B2 | 6/2018 | Li et al. | |
| 10,159,446 B2 | 12/2018 | Dickerson | |
| 10,166,406 B2 | 1/2019 | Nord et al. | |
| 10,251,629 B2 | 4/2019 | Belt et al. | |
| 10,265,543 B2 | 4/2019 | Bharat et al. | |
| 10,286,228 B2 | 5/2019 | Bharat et al. | |
| 10,315,049 B2 | 6/2019 | Gauthier et al. | |
| 10,342,558 B2 | 7/2019 | Steckner et al. | |
| 10,363,439 B2 | 7/2019 | Amaldi | |
| 10,485,992 B2 | 11/2019 | Heese et al. | |
| 10,500,418 B2 | 12/2019 | Filiberti et al. | |
| 10,548,496 B2 | 2/2020 | Gijsbers et al. | |
| 10,646,188 B2 | 5/2020 | Mostafavi et al. | |
| 10,792,511 B2 | 10/2020 | Pankratov et al. | |
| 10,974,069 B2 | 4/2021 | Maguire et al. | |
| 11,097,127 B2 | 8/2021 | Sumanaweera et al. | |
| 11,272,902 B2 | 3/2022 | Geelen et al. | |
| 11,298,565 B2 | 4/2022 | Garonna et al. | |
| 11,406,845 B2 | 8/2022 | Robinson et al. | |
| 11,506,801 B2 | 11/2022 | Sauli et al. | |
| 11,857,808 B2 | 1/2024 | Packer et al. | |
| 11,951,327 B2 | 4/2024 | Garonna et al. | |
| 2002/0072674 A1 | 6/2002 | Criton et al. | |
| 2002/0095197 A1 | 7/2002 | Lardo et al. | |
| 2004/0015075 A1 | 1/2004 | Kimchy et al. | |
| 2004/0162596 A1 | 8/2004 | Altshuler et al. | |
| 2004/0260142 A1 | 12/2004 | Lovoi | |
| 2004/0267113 A1 | 12/2004 | Thomson | |
| 2005/0171396 A1 | 8/2005 | Pankratov et al. | |
| 2006/0039591 A1 | 2/2006 | Zettel et al. | |
| 2006/0074292 A1 | 4/2006 | Thomson et al. | |
| 2006/0224053 A1 | 10/2006 | Black et al. | |
| 2006/0241443 A1 | 10/2006 | Whitmore et al. | |
| 2006/0291621 A1 | 12/2006 | Yan et al. | |
| 2007/0041499 A1 | 2/2007 | Lu et al. | |
| 2008/0021300 A1 | 1/2008 | Allison | |
| 2008/0023644 A1 | 1/2008 | Pedroni | |
| 2008/0081982 A1 | 4/2008 | Simon et al. | |
| 2008/0177279 A1* | 7/2008 | Sumanaweera | A61N 5/1068 901/41 |
| 2008/0177280 A1 | 7/2008 | Adler et al. | |
| 2008/0191142 A1 | 8/2008 | Pedroni | |
| 2008/0221382 A1 | 9/2008 | Karshafian et al. | |
| 2008/0317204 A1 | 12/2008 | Sumanaweera et al. | |
| 2009/0074278 A1 | 3/2009 | Beaulieu et al. | |
| 2009/0076373 A1 | 3/2009 | Maschke | |
| 2009/0080610 A1 | 3/2009 | Sumanaweera et al. | |
| 2009/0180589 A1 | 7/2009 | Wang et al. | |
| 2009/0206269 A1 | 8/2009 | Kraft et al. | |
| 2009/0234237 A1 | 9/2009 | Ross et al. | |
| 2009/0238404 A1 | 9/2009 | Orderud et al. | |
| 2009/0253102 A1 | 10/2009 | Porikli et al. | |
| 2009/0257557 A1 | 10/2009 | Sumanaweera et al. | |
| 2009/0306515 A1 | 12/2009 | Matsumura et al. | |
| 2010/0016744 A1 | 1/2010 | Brost et al. | |
| 2010/0016765 A1 | 1/2010 | Hall et al. | |
| 2010/0137709 A1 | 6/2010 | Gardner et al. | |
| 2010/0145358 A1 | 6/2010 | Maschke | |
| 2010/0183120 A1 | 7/2010 | Nord et al. | |
| 2010/0217139 A1 | 8/2010 | Pinter et al. | |
| 2010/0239066 A1 | 9/2010 | Fahrig et al. | |
| 2010/0266099 A1 | 10/2010 | Busch et al. | |
| 2010/0282983 A1 | 11/2010 | Wright et al. | |
| 2010/0301235 A1 | 12/2010 | Bert et al. | |
| 2010/0317968 A1 | 12/2010 | Wright et al. | |
| 2011/0038516 A1 | 2/2011 | Koehler et al. | |
| 2011/0107270 A1 | 5/2011 | Wang et al. | |
| 2011/0137158 A1 | 6/2011 | Sumanaweera et al. | |
| 2011/0160566 A1 | 6/2011 | Petropoulos et al. | |
| 2011/0166407 A1 | 7/2011 | Sumanaweera et al. | |
| 2011/0166408 A1 | 7/2011 | Sumanaweera et al. | |
| 2011/0185503 A1 | 8/2011 | Yan | |
| 2011/0190629 A1 | 8/2011 | Guenther et al. | |
| 2011/0218438 A1 | 9/2011 | Hsieh et al. | |
| 2012/0004518 A1 | 1/2012 | D'Souza et al. | |
| 2012/0014501 A1 | 1/2012 | Pelc et al. | |
| 2012/0083645 A1 | 4/2012 | Sun et al. | |
| 2012/0134233 A1 | 5/2012 | Lin et al. | |
| 2012/0146641 A1 | 6/2012 | Wu et al. | |
| 2012/0181428 A1 | 7/2012 | Bert et al. | |
| 2012/0241635 A1 | 9/2012 | Luechtenborg et al. | |
| 2012/0292534 A1 | 11/2012 | Geneser et al. | |
| 2012/0316423 A1 | 12/2012 | Raleigh et al. | |
| 2012/0323233 A1 | 12/2012 | Maguire et al. | |
| 2013/0035682 A1 | 2/2013 | Weil | |
| 2013/0053617 A1 | 2/2013 | Pu et al. | |
| 2013/0079645 A1 | 3/2013 | Amirana et al. | |
| 2013/0211482 A1 | 8/2013 | Piipponen et al. | |
| 2013/0237822 A1 | 9/2013 | Gross et al. | |
| 2013/0336450 A1 | 12/2013 | Kyriakou et al. | |
| 2014/0005463 A1 | 1/2014 | Jongen | |
| 2014/0107390 A1 | 4/2014 | Brown et al. | |
| 2014/0107435 A1 | 4/2014 | Sharf et al. | |
| 2014/0316247 A1 | 10/2014 | Hwang et al. | |
| 2014/0343401 A1 | 11/2014 | Huber et al. | |
| 2015/0004561 A1 | 1/2015 | Koehler | |
| 2015/0080634 A1 | 3/2015 | Huber et al. | |

(56) References Cited

U.S. PATENT DOCUMENTS

| | | |
|---|---|---|
| 2015/0092907 A1 | 4/2015 | Dong et al. |
| 2015/0112197 A1 | 4/2015 | Bharat |
| 2015/0146955 A1 | 5/2015 | Dong et al. |
| 2015/0150643 A1 | 6/2015 | Trayanova et al. |
| 2015/0182760 A1 | 7/2015 | Raleigh et al. |
| 2015/0209599 A1 | 7/2015 | Schlosser et al. |
| 2015/0290472 A1 | 10/2015 | Maguire et al. |
| 2015/0331118 A1 | 11/2015 | Iltis |
| 2015/0343238 A1 | 12/2015 | Balakin |
| 2015/0371420 A1 | 12/2015 | Yerushalmy et al. |
| 2016/0000409 A1 | 1/2016 | Bruder et al. |
| 2016/0035108 A1 | 2/2016 | Yu et al. |
| 2016/0058368 A1 | 3/2016 | Swaminathan et al. |
| 2016/0074674 A1 | 3/2016 | Kohli et al. |
| 2016/0082284 A1 | 3/2016 | Ooga et al. |
| 2016/0114189 A1 | 4/2016 | Mihailescu |
| 2016/0117850 A1 | 4/2016 | Jin et al. |
| 2016/0121142 A1 | 5/2016 | Zhang et al. |
| 2016/0125625 A1 | 5/2016 | Kim et al. |
| 2016/0184610 A1 | 6/2016 | Porikli |
| 2016/0324499 A1 | 11/2016 | Sen Sharma et al. |
| 2016/0331262 A1 | 11/2016 | Kuck et al. |
| 2016/0338676 A1 | 11/2016 | Berger et al. |
| 2016/0339271 A1 | 11/2016 | Bach et al. |
| 2016/0371862 A1 | 12/2016 | Silver et al. |
| 2017/0014642 A1 | 1/2017 | An et al. |
| 2017/0014645 A1 | 1/2017 | Foo et al. |
| 2017/0042515 A1 | 2/2017 | Schwartz et al. |
| 2017/0080253 A1 | 3/2017 | Clayton |
| 2017/0095197 A1 | 4/2017 | Kleiner et al. |
| 2017/0106208 A1 | 4/2017 | Gauthier et al. |
| 2017/0128744 A1 | 5/2017 | Adler et al. |
| 2017/0203123 A1 | 7/2017 | Requardt et al. |
| 2018/0153467 A1 | 6/2018 | Lichtenstein et al. |
| 2018/0185671 A1 | 7/2018 | Filiberti et al. |
| 2018/0214713 A1 | 8/2018 | Dehghan et al. |
| 2018/0243584 A1 | 8/2018 | Nord et al. |
| 2018/0252825 A1 | 9/2018 | Benlloch Baviera et al. |
| 2018/0318606 A1 | 11/2018 | Robinson et al. |
| 2019/0099621 A1 | 4/2019 | Koehl et al. |
| 2019/0164288 A1 | 5/2019 | Wang et al. |
| 2019/0344098 A1 | 11/2019 | Maguire et al. |
| 2019/0351254 A1 | 11/2019 | Sumanaweera et al. |
| 2019/0380670 A1 | 12/2019 | Hofmann et al. |
| 2020/0016429 A1 | 1/2020 | Maguire et al. |
| 2020/0090345 A1 | 3/2020 | Krebs et al. |
| 2020/0113546 A1 | 4/2020 | Madore et al. |
| 2020/0151921 A1 | 5/2020 | Schildkraut |
| 2020/0179722 A1 | 6/2020 | Packer et al. |
| 2021/0012544 A1 | 1/2021 | Lee et al. |
| 2021/0015454 A1 | 1/2021 | Puleo et al. |
| 2021/0065414 A1 | 3/2021 | Do |
| 2022/0183657 A1 | 6/2022 | McLaughlin et al. |

FOREIGN PATENT DOCUMENTS

| | | |
|---|---|---|
| CN | 1672651 A | 9/2005 |
| CN | 101268467 A | 9/2008 |
| CN | 101600473 A | 12/2009 |
| CN | 102119586 A | 7/2011 |
| CN | 102196768 A | 9/2011 |
| CN | 102510735 A | 6/2012 |
| CN | 102781359 A | 11/2012 |
| CN | 103180015 A | 6/2013 |
| CN | 103279929 A | 9/2013 |
| CN | 104349817 A | 2/2015 |
| CN | 105813691 A | 7/2016 |
| CN | 106291656 A | 1/2017 |
| CN | 107730455 A | 2/2018 |
| CN | 108022272 A | 5/2018 |
| CN | 111223156 A | 6/2020 |
| DE | 102013102920 A1 | 9/2014 |
| DE | 102013112573 A1 | 6/2015 |
| DE | 102014217966 A1 | 3/2016 |
| EP | 0327459 B1 | 9/1992 |
| EP | 2140913 A1 | 1/2010 |
| EP | 2290406 A2 | 3/2011 |
| EP | 2523623 A1 | 11/2012 |
| EP | 2942081 A1 | 11/2015 |
| EP | 2950119 A1 | 12/2015 |
| EP | 3036978 A1 | 6/2016 |
| FR | 2930995 A1 | 11/2009 |
| FR | 3058249 A3 | 5/2018 |
| JP | 2005095640 A | 4/2005 |
| JP | 2006113061 A | 4/2006 |
| JP | 2007047066 A | 2/2007 |
| JP | 2007526010 A | 9/2007 |
| JP | 2010540050 A | 12/2010 |
| JP | 2012533364 A | 12/2012 |
| JP | 2016214438 A | 12/2016 |
| KR | 20110040164 A | 4/2011 |
| WO | WO-2009111783 A2 | 9/2009 |
| WO | WO-2011012154 A1 | 2/2011 |
| WO | WO-2011021410 A1 | 2/2011 |
| WO | WO-2012104416 A1 | 8/2012 |
| WO | WO-2012152938 A2 | 11/2012 |
| WO | WO-2012154219 A2 | 11/2012 |
| WO | WO-2013034709 A1 | 3/2013 |
| WO | WO-2013129811 A1 | 9/2013 |
| WO | WO-2013179221 A1 | 12/2013 |
| WO | WO-2015025203 A1 | 2/2015 |
| WO | WO-2015040225 A1 | 3/2015 |
| WO | WO-2015053737 A1 | 4/2015 |
| WO | WO-2016193929 A2 | 12/2016 |
| WO | WO-2017066358 A1 | 4/2017 |
| WO | WO-2017078757 A1 | 5/2017 |
| WO | WO-2017156113 A1 | 9/2017 |
| WO | WO-2019017752 A1 | 1/2019 |
| WO | WO-2019096943 A1 | 5/2019 |
| WO | WO-2020033355 A1 | 2/2020 |
| WO | WO-2020075106 A2 | 4/2020 |
| WO | WO-2020142397 A1 | 7/2020 |
| WO | WO-2020212573 A1 | 10/2020 |
| WO | WO 01/26569 | 4/2021 |
| WO | WO-2021094824 A1 | 5/2021 |
| WO | WO-2022136925 A1 | 6/2022 |
| WO | WO-2024062307 A1 | 3/2024 |

OTHER PUBLICATIONS

Kingma et al., "Adam: A Method for Stochastic Optimization," 3rd International Conference on Learning Representations, ICLR 2015— Conference Track Proceedings, 15 pages, 2015.

Devries et al., "Improved Regularization of Convolutional Neural Networks with Cutout," 8 pages, 2017.

Bai et al., "An Empirical Evaluation of Generic Convolutional and Recurrent Networks for Sequence Modeling," arXiv Prepr. arXiv1803.01271, 14 pages, 2018.

Fiorito et al., "Detection of Cardiac Events in Echocardiography using 3D Convolutional Recurrent Neural Networks," Ultrasonics Symposium (IUS), 2018 IEEE International, 4 pages, 2018.

Prall et al. "Treatment of arrhythmias by external charged particle beams: a Langendorff feasibility study" Biomed. Eng.-Biomed. Tech. 60(2) pp. 147-156 (2015).

Lehmann et al. "Feasbility Study on Cardia Arrhythmia Ablation Using High-Energy Heavy Ion Beams" Nature/ Scientific Reports 6:38895 | DOI: 10.1038/srep38895 (2016) 13 pages.

Achenbach S., et al., "Noninvasive Coronary Angiography by Retrospectively ECG-Gated Multislice Spiral CT," Circulation, 102(23):2823-2828 (Dec. 2000).

Asirvatham S.J., "Advances in Catheter Ablation: A Burning Trail!," Indian Heart Journal, 2011, pp. 379-385.

Baker, et al., "Prostate Displacement During Transabdominal Ultrasound Image-Guided Radiotherapy Assessed By Real-Time Four-dimensional Transperineal Monitoring," Acta Oncologica, 2015, vol. 54, No. 9, pp. 1508-1514.

Beddar A.S., et al., "Correlation Between Internal Fiducial Tumor Motion and External Marker Motion for Liver Tumors Imaged With 4D-CT," International Journal of Radiation Oncology, Biology, Physics, vol. 67(2):630-638 (Feb. 2007).

(56) References Cited

OTHER PUBLICATIONS

Beltrame P., et al., "Construction and Tests of Demonstrator Modules for a 3-D Axial PET System for Brain or Small Animal Imaging," Nuclear Instruments and Methods in Physics Research A, 2011, vol. 636, pp. S226-S230, Available Online May 5, 2010.
Bert C., et al., "Motion in Radiotherapy: Particle Therapy," Physics in Medicine and Biology, 2011, vol. 56, pp. R113-R44.
Bertholet, et al., "Real-Time Intrafraction Motion Monitoring In External Beam Radiotherapy," Physics in Medicine, 2019, vol. 64, No. 15.
Blanck O., et al., "Dose-Escalation Study for Cardiac Radiosurgery in a Porcine Model," Int J Radiat Oncol Biol Phys., vol. 89:590-598 (Dec. 2014).
Blanck, "Radiosurgery for Ventricular Tachycardia: Preclinical and Clinical Evidence and Study Design for a German Multi-Center Multi-Platform Feasibility Trial (RAVENTA)," Clinical Research in Cardiology, 09:1319-1332 (Nov. 2020).
Boas F.E., et al., "Evaluation of Two Iterative Techniques for Reducing Metal Artifacts in Computed Tomography," Radiology, Jun. 2011, vol. 259, No. 3, pp. 894-902.
Bode F., et al., "Pulmonary Vein Isolation by Radiosurgery: Implications for Non-Invasive Treatment of Atrial Fibrillation," Europace, vol. 17:1868-1874 (Mar. 2015).
Braem A., et al., "AX-PET: A Novel PET Detector Concept with Full 3D Reconstruction," Nuclear Instruments and Methods in Physics Research A, 2009, vol. 610, pp. 192-195, Available Online May 29, 2009.
Calkins H., et al., "2012 HRS/EHRA/ECAS Expert Consensus Statement on Catheter and Surgical Ablation of Atrial Fibrillation: Recommendations for Patient Selection Procedural Techniques, Patient Management and Follow-Up, Definitions, Endpoints, and Research Trial Design," Heart Rhythm, 2012, vol. 9(4):632-696(e21) (Apr. 2012).
Cappato R., et al., "Updated Worldwide Survey on the Methods, Efficacy, and Safety of Catheter Ablation for Human Atrial Fibrillation," Circulation: Arrhythmia and Electrophysiology, 2010, vol. 3, pp. 32-38, DOI: 10.1161/CIRCEP.109.859116.
Casella C., et al., "A High Resolution TOF-PET Concept With Axial Geometry and Digital SiPM Readout," Nuclear Instruments and Methods in Physics Research A, 2014, vol. 736, pp. 161-168.
Chaudhri, et al., "SU-E-T-334: Clinical Implementation of Gating and Dose Verification with Scanned Ion Beams at HIT," Medical Physics, The American Association of Physicists in Medicine, 39(Issue 6—Part 15):3780-3781 (Jun. 2012).
Che, et al., "Ultrasound Registration: A Review," Methods, 115:128-143 (Feb. 2017).
Constantinescu A., et al., "Catheter-Free Ablation of Atrial Fibrillation: Further Planning Studies in Patient Data Using a Scanned Carbon Ion Beam for Pulmonary Vein Isolation, MP04- 02," Hearth Rhythm, May 2014, vol. 11 No. 5, Supplement.
Constantinescu A., et al., "Planning Studies for Non-Invasive Isolation of the Pulmonary Veins with a Scanned Carbon Ion Beam," Heart Rhythm, 2013, vol. 10, p. S33.
Constantinescu A., et al., "Treatment Planning Studies in Patient Data with Scanned Carbon Ion Beams for Catheter-Free Ablation of Atrial Fibrillation," Journal of Cardiovascular Electrophysiology, 2016, vol. 27, No. 3, pp. 335-344.
De Luca, et al., "The 2014 Liver Ultrasound Tracking Benchmark," Physics in Medicine & Biology, 60(14):5571 (Jul. 2015).
Degiovanni A., et al., "Design of a Fast-Cycling High-Gradient Rotating Linac For Protontherapy," Proceedings of IPAC, Shanghai, China THPWA008, 2013, pp. 3642-3644.
Deisher A., et al., "Catheter-Free Ablation With External Photon Radiation: Treatment Planning, Delivery Considerations, and Correlation of Effects With Delivered Dose," Heart Rhythm, May 2015, vol. 12, No. 5, Supplement.
Del Carpio Munoz F., et al., "Three-Dimensional Mapping of Cardiac Arrhythmias: What do the Colors Really Mean?," Circulation Arrhythmia and Electrophysiology, Dec. 2010, vol. 3, No. 6, pp. e6-11.

Deneke T., et al., "Silent Cerebral Events/Lesions Related to Atrial Fibrillation Ablation: A Clinical Review," Journal of Cardiovascular Electrophysiology, 2015, vol. 26, pp. 455-463, DOI: 10.1111/jce.12608.
Depuydt, et al., "Treating Patients With Real-Time Tumor Tracking Using the Vero Gimbaled Linac System: Implementation and First Review," Radiotherapy and Oncology, 2014, vol. 112, No. 3, pp. 343-351.
Dickfeld T., et al., "MRI-Guided Ventricular Tachycardia Ablation: Integration of Late Gadolinium-Enhanced 3D Scar in Patients with Implantable Cardioverter-Defibrillators," Circulation Arrhythmia and Electrophysiology, 2011, vol. 4, pp. 172-184. DOI: 10.1161/CIRCEP.110.958744.
Dieterich S., et al., "Respiratory Motion Management for External Beam Radiotherapy," Practical Radiation Oncology Physics, Elsevier Inc., 2016, pp. 252-263.
Dinov B., et al., "Early Referral for Ablation of Scar-Related Ventricular Tachycardia is Associated with Improved Acute and Long-Term Outcomes: Results from the Heart Center of Leipzig Ventricular Tachycardia Registry," Circulation Arrhythmia and Electrophysiology, 2014, vol. 7, pp. 1144-1151, DOI: 10.1161/CIRCEP.114.001953.
Extended European Search Report for European Application No. 18851934.2, mailed Sep. 15, 2021, 13 Pages.
Fayad, et al., "Technical Note: Correlation Of Respiratory Motion Between External Patient Surface and Internal Anatomical Landmarks," Medical Physics, 38(6):3157-3164 (Jun. 2011).
Fishbein M.C., et al., Early Phase Acute Myocardial Infarct Size Quantification: Validation of the Triphenyl Tetrazolium Chloride Tissue Enzyme Staining Technique, American Heart Journal, 1981, vol. 101, pp. 593-600.
Fontanarosa, et al., "Review Of Ultrasound Image Guidance In External Beam Radiotherapy: I. Treatment Planning and Inter-Fraction Motion Management," Physics in Medicine & Biology, 60(3):R77-R114 (Jan. 2015).
Franceschi F., et al., "Histopathological Effects and Evolution of Transvenous B-Radiation Applications in Right and Left Atria: An Animal Study," Europace, 2012, vol. 14, pp. 745-751, DOI: 10.1093/europace/eur351.
Ge J., et al., "Planning 4-Dimensional Computed Tomography (4DCT) Cannot Adequately Represent Daily Intrafractional Motion of Abdominal Tumors," International Journal of Radiation Oncology, Biology, Physics, vol. 85(4):999-1005 (Mar. 2013).
Gerstenfeld E.P., "Recurrent Ventricular Tachycardia after Catheter Ablation in Post-Infarct Cardiomyopathy: "Failure" of Ablation or Progression of the Substrate?," Journal of the American College of Cardiology, 2013, vol. 61, pp. 74-76, DOI: 10.1016/j.jacc.2012.07.057.
Graeff C., et al., "A 4D-Optimization Concept for Scanned Ion Beam Therapy," Radiotherapy and Oncology, Available Online Oct. 31, 2013, vol. 109, pp. 419-424.
Graeff C., et al., "Motion Mitigation in Intensity Modulated Particle Therapy by Internal Target Volumes Covering Range Changes," Medical Physics, 2012, vol. 39, pp. 6004-6013.
Graeff, et al., "Noninvasive Cardiac Arrhythmia Ablation With Particle Beams," Medical Physics, vol. 45, No. 11 (Nov. 2018).
Grimm J., et al., "Dose Tolerance Limits and Dose vol. Histogram Evaluation for Stereotactic Body Radiotherapy," Journal of Applied Clinical Medical Physics, vol. 12(2): 267-292 (Jan. 2011).
Guerra P.G., et al., "Beta-Radiation for the Creation of Linear Lesions in the Canine Atrium," Circulation, 2004, vol. 110, pp. 911-914, DOI: 10.1161/01.CIR.0000139865.39885.03.
Haberer T., et al., "Magnetic Scanning System for Heavy ion Therapy," Nuclear Instruments and Methods A, 1993, vol. 330, pp. 296-305.
Hartman J., et al., "Dosimetric Feasibility of Intensity Modulated Proton Therapy in a Transverse Magnetic Field of 1.5 T," Physics in Medicine and Biology, 2015, vol. 60, pp. 5955-5969.
Hoogeman, et al., "Clinical Accuracy of the Respiratory Tumor Tracking System of the Cyberknife: Assessment by Analysis of Log Files," International Journal of Radiation Oncology, Biology, Physics, 2009, vol. 74, No. 1, pp. 297-303, DOI: 10.1016/j.ijrobp.2008.12.041, XP026037471.

(56) References Cited

OTHER PUBLICATIONS

Iguchi T., et al., "Development of Compact Compton Gamma Camera for Non-Destructive Detection and Location of Hidden Explosives with Neutron Induced Prompt Gamma-Ray Imaging," Nuclear Science Symposium Conference Record, IEE Wyndham El Conquistador Resort, Puerto Rico, Piscataway, NJ, USA, IEEE, Oct. 23-29, 2005, vol. 2, pp. 735-739, DOI:10.1109/NSSMIC.2005. 1596362, ISBN 978-0-7803-9221-2, XP010895599.

International Search Report & Written Opinion dated Dec. 11, 2023 in Int'l PCT Patent Appl. Serial No. PCT/IB2023/058539 (0710).

International Search Report and Written Opinion for International Application No. PCT/EP2018/081455, mailed Feb. 12, 2019, 13 Pages.

International Search Report and Written Opinion for International Application No. PCT/IB2019/058638, mailed Jun. 25, 2020, 17 Pages.

International Search Report and Written Opinion for International Application No. PCT/IB2020/000930, mailed Apr. 9, 2021, 11 Pages.

International Search Report and Written Opinion for International Application No. PCT/IB2021/000922, mailed Apr. 19, 2022, 15 Pages.

International Search Report and Written Opinion for International Application No. PCT/US2018/049114, mailed Nov. 21, 2018, 09 Pages.

Ipsen, et al., "Radiotherapy Beyond Cancer: Target Localization in Real-time MRI and Treatment Planning for Cardiac Radiosurgery," Medical Physics, vol. 41(12):120702_1-120702_8 (Dec. 2014).

Ipsen, et al., "Target Tracking Accuracy and Latency With Different 4D Ultrasound Systems—A Robotic Phantom Study," Current Directions in Biomedical Engineering, 6(1):20200038 (Sep. 2020).

Ipsen, S., "See What You Treat: 4d Ultrasound Imaging for Real Time Motion Compensation in the Liver," PHD Thesis University of Luebeck, pp. 1-142 (Nov. 2019).

Kachelriess M., et al., "ECG-Correlated Image Reconstruction from Subsecond Multi-Slice Spiral CT Scans of the Heart," Medical Physics, 2000, vol. 27, pp. 1881-1902.

Keall et al., "The Management of respiratory motion in radiation on oncology report of AAPM Task Group $76^{a)}$," Med. Phys., vol. 33(10):3874-3900 (Oct. 2006).

Keall P.J, et al., "The First Clinical Implementation of Electromagnetic Transponder-Guided MLC Tracking," Medical Physics, 2014, vol. 41: 020702.

Keall P.J., et al., "The First Clinical Treatment with Kilovoltage Intrafraction Monitoring (Kim): A Real-Time Image Guidance Method," Medical Physics, 2015, vol. 42, pp. 354-358.

Khalil, et al., "An Overview on Image Registration Techniques for Cardiac Diagnosis and Treatment," Cardiology Research and Practice, 2018, Article ID 1437125, 15 pages, https://doi.org/10.1155/2018/1437125.

Kincaid, et al., "Investigation of Gated Cone-Beam CT to Reduce Respiratory Motion Blurring," Medical Physics, 40(4):041717 (Apr. 2013).

Koike Y., et al., "Deep Learning-Based Metal Artifact Reduction Using Cycle-Consistent Adversarial Network for Intensity-Modulated Head and Neck Radiation Therapy Treatment Planning," Physica Medica, Sep. 7, 2020, vol. 78, pp. 8-14.

Krimmer J., et al., "Prompt-Gamma Monitoring in Hadrontherapy: A Review," Nuclear Instruments and Methods in Physics Research A, 2018, vol. 878, pp. 58-73, Available online Aug. 12, 2017.

Kumar S., et al., "Effect of Respiration on Catheter-Tissue Contact Force during Ablation of Atrial Arrhythmias," Heart Rhythm, vol. 9(7):1041-1047e1 (Jul. 2012).

Kuntz J., et al., "Fully Automated Intrinsic Respiratory and Cardiac Gating for Small Animal CT," Physics in Medicine and Biology, vol. 55:2069-2085 (Apr. 2010).

Lachaine, et al., "Intrafractional Prostate Motion Management With the Clarity Autoscan System," Medical Physics International Journal, 1(1):72-80 (2013).

Lehmann H.I., et al., "Atrioventricular Node Ablation in Langendorffperfused Porcine Hearts using Carbon Ion Particle Therapy: Methods and an in Vivo Feasibility Investigation for Catheter-Free Ablation of Cardiac Arrhythmias," Circulation Arrhythmia and Electrophysiology, Apr. 2015, vol. 8, pp. 429-438, DOI: 10.1161/ CIRCEP.114.002436.

Lehmann H.I., et al., "Biophysics of Tissue Ablation in Catheter-Free Ablation With Carbon Ion Beams," vol. 13:(5):AB29-05 S67 (May 1016).

Lehmann H.I., et al., "Delineation of Target Locations and Organs at Risk for Particle Beam Therapy: Atlas for Extracorporeal CT-Based Ablation of Cardiac Tissue," Heart Rhythm, May 2017 vol. 11, No. 5, Supplement.

Lehmann H.I., et al., "External Arrhythmia Ablation using Photon Beams: Ablation of the Atrioventricular Junction in an Intact Animal Model," Circulation: Arrhythmia and Electrophysiology, Apr. 2017, vol. 10, No. 4 (e004304).

Lehmann H.I., et al., "In-Beam PET Verification of Catheter-Free Arrhythmia Ablation by Scanned Carbon-12 Ion Beam Irradiation," Circulation, 2015, vol. 132, Supplement. 3, p. A12443.

Li, et al., Comparative Quantitative Analysis of Robotic Ultrasound Image Calibration Methods, 2021 20th International Conference on Advanced Robotics (ICAR), IEEE, pp. 511-516.

Lin M.H., et al., "4D Patient Dose Reconstruction using Online Measured EPID Cine Images for Lung SBRT Treatment Validation," Medical Physics, 2012, vol. 39, pp. 5949-5958.

Lis M., et al., "A Modular Dose Delivery System for Treating Moving Targets With Scanned Ion Beams: Performance and Safety Characteristics, and Preliminary Tests," Physica Medica, 2020, vol. 76, pp. 307-316.

Luzhbin D., et al., "Model Image-Based Metal Artifact Reduction for Computed Tomography," Journal of Digital Imaging, 2020, vol. 33, pp. 71-82.

Maguire., et al., "First-in-Man Cardiac Radiosurgery for Atrial Arrhythmia," International Journal of Radiation Oncology, Biology, Physics, 96(2):E504-5 (Oct. 2016).

Maguire P., et al., "Cardiac Radiosurgery (CyberHeart) for Treatment of Arrhythmia: Physiologic and Histopathologic Correlation in the Porcine Model," Cureus, 3(8):(e32) (Aug. 2011).

Nakao M., et al., "Regularized Three-Dimensional Generative Adversarial Nets for Unsupervised Metal Artifact Reduction in Head and Neck CT Images," IEEE Access, Digital Object Identifier, Jun. 12, 2020, vol. 8, pp. 109453-109465.

Nankali, et al., "Geometric And Dosimetric Comparison of Four Intrafraction Motion Adaptation Strategies for Stereotactic Liver Radiotherapy," Physics in Medicine & Biology, 63(14):145010 (Jul. 2018).

Ng J., et al., "Mapping of Dominant Activation Directions in a Canine Rapid Atrial Pacing Model of Atrial Fibrillation," Heart Rhythm Session, May 12, 2017.

O'Shea, et al., "Review of Ultrasound Image Guidance in External Beam Radiotherapy Part II: Intra-Fraction Motion Management and Novel Applications," Physics in Medicine & Biology, 2016, vol. 61, No. 8, DOI: 10.1088/0031-9155/61/8/R90, XP020303407.

Okumura Y., et al., "Three-Dimensional Ultrasound for Image-Guided Mapping and Intervention: Methods, Quantitative Validation, and Clinical Feasibility of a Novel Multimodality Image Mapping System," Circulation Arrhythmia Electrophysiology, 2008, vol. 1, pp. 110-119, DOI: 10.1161/ CIRCEP.108.769935.

Ortega P.G., et al., "Noise Evaluation of Compton Camera Imaging for Proton Therapy," Physics in Medicine and Biology, Institute of Physics Publishing and Engineering in Medicine, Bristol, GB, Feb. 6, 2015, vol. 60, No. 5, pp. 1845-1863, DOI: 10.1088/0031-9155/60/5/1845, ISSN 0031-9155.

Ortmaier T., et al., "Motion Estimation in Beating Heart Surgery," IEEE Transactions on Biomedical Engineering, 2005, vol. 52, pp. 1729-1740.

Pan J., et al., "A Real-Time QRS Detection Algorithm," IEEE Transactions on Biomedical Engineering, Mar. 1985, vol. BME-32, No. 3, pp. 230-236.

Partial Supplementary European Search Report for European Application No. 18851934.2, mailed Apr. 22, 2021, 11 Pages.

(56) References Cited

OTHER PUBLICATIONS

Perali I., et al., "Prompt Gamma Imaging of Proton Pencil Beams at Clinical Dose Rate," Institute of Physics and Engineering in Medicine, Physics in Medicine and Biology, Sep. 10, 2014, vol. 59, pp. 5849-5871.
Peulen H., et al., "Mid-Ventilation Based PTV Margins in Stereotactic Body Radiotherapy (SBRT): A Clinical Evaluation," Radiotherapy and Oncology, vol. 110:(3):511-516, DOI: 10.1016/j.radonc.2014.01.010 (Mar. 2014).
Pfanner F., et al. "Monitoring Cardiac Motion in CT using a Continuous Wave Radar Embedded in the Patient Table," Medical Physics, 2014, vol. 41: 081908.
Pfanner F., et al., "Monitoring internal organ motion with continuous wave radar in CT," Medical Physics, 2013, vol. 40: 091915.
Piersanti L., et al., Measurement of Charged Particle Yields from PMMA Irradiated by a 220 MeV/u (12)C Beam, Physics in Medicine and Biology, 2014, vol. 59, pp. 1857-1872.
Poon, et al., "Technical Note: Cardiac Synchronized Volumetric Modulated Arc Therapy for Stereotactic Arrhythmia Radioablation -Proof of Principle," Medical Physics, vol. 47(8):3567-3572 (Aug. 2020).
Poulsen P.R., et al., "A Method of Dose Reconstruction for Moving Targets Compatible with Dynamic Treatments," Medical Physics, vol. 39(10):6237-6246 (Oct. 2012).
Poulsen P.R., et al., "Kilovoltage Intrafraction Motion Monitoring and Target Dose Reconstruction for Stereotactic Volumetric Modulated Arc Therapy of Tumors in the Liver," Radiotherapy and Oncology, 2014, vol. 111, pp. 424-430.
Prall M., et al., "Ion Beam Tracking Using Ultrasound Motion Detection," Medical Physics, 41(4):041708-1-041708-5 (Apr. 2014).
Pérez-Castellano N., et al., "Pathological Effects of Pulmonary Vein Beta-Radiation in a Swine Model," Journal of Cardiovascular Electrophysiology, 2006, vol. 17, pp. 662-669, DOI: 10.1111/j.1540-8167.2006.00462.x.
Queiros, et al., "Fast Left Ventricle Tracking Using Localized Anatomical Affine Optical Flow," International Journal for Numerical Methods in Biomedical Engineering, 33(11):e2871 (Nov. 2017).
Raaymakers B.W., et al., "Integrating a 1.5 T MRI Scanner With A 6 MV Accelerator: Proof of Concept," Physics in Medicine and Biology, 54(12):N229-N37 (May 2009).
Ravkilde T., et al., "Time-Resolved Dose Distributions to Moving Targets During Volumetric Modulated Arc Therapy With and Without Dynamic MLC Tracking," Medical Physics, 2013, 40(11):111723-1-111723-8 (Nov. 2013).
Rettmann M.E., et al., "Analysis of Left Atrial Respiratory and Cardiac Motion for Cardiac Ablation Therapy," Medical Imaging 2015: Image-Guided Procedures, Robotic Interventions, and Modeling, 9415:651-656 ) Mar. 2015.
Rettmann M.E., et al., "Centerline Tracking for Quantification of Reverse Structural Remodeling of the Pulmonary Veins Following Cardiac Ablation Therapy," Academic Radiology, 19(11):1332-1344 (Nov. 2012).
Richter C., et al., "First Clinical Application of a Prompt Gamma Based in Vivo Proton Range Verification System," Radiotherapy and Oncology, vol. 118(2):232-237 (Feb. 2016).
Richter D., et al., "ECG-Based 4d-Dose Reconstruction of Cardiac Arrhythmia Ablation With Carbon Ion Beams: Application in a Porcine Model," Physics in Medicine and Biology, Aug. 4, 2017, vol. 62, No. 17, p. 6869.
Richter D., et al., "Four-Dimensional Patient Dose Reconstruction for Scanned Ion Beam Therapy of Moving Liver Tumors," International Journal of Radiation Oncology, Biology, Physics, 2014, vol. 89, pp. 175-181.
Richter D., et al., "Residual Motion Mitigation in Scanned Carbon Ion Beam Therapy of Liver Tumors Using Enlarged Pencil Beam Overlap," Radiotherapy and Oncology, vol. 113, pp. 290-295 (Nov. 2014).
Richter D., et al., "Upgrade and Benchmarking of a 4D Treatment Planning System for Scanned Ion Beam Therapy," Medical Physics, vol. 40:051722 (May 2013).
Robinson, et al., "An Evaluation of the Clarity 3D Ultrasound System for Prostate Localization," Journal of Applied Clinical Medical Physics, 13(4):100-112 (Jul. 2012).
Roujol, et al., "Characterization of Respiratory and Cardiac Motion From Electro-Anatomical Mapping Data for Improved Fusion of MRI to Left Ventricular Electrograms," PloS One, 2013, vol. 8, No. 11, p. e78852.
Saint-Gobain Ceramics & Plastics Inc: "Scintillation Materials and Assemblies, About Saint-Gobain Crystals," Saint-Gobain Crystals Handbook, 2004-2019, 12 Pages.
Sauli F., "Radiation Imaging with Gaseous Detectors," Nuclear Instruments and Methods in Physics Research A, 2018, vol. 878, pp. 1-9.
Scandurra D., et al., "Assessing the Quality of Proton PBS Treatment Delivery Using Machine Log Files: Comprehensive Analysis of Clinical Treatments Delivered at PSI Gantry 2," Physics in Medicine and Biology, vol. 61, pp. 1171-1181 (Jan. 2016).
Schardt D., et al., "Heavy-Ion Tumor Therapy: Physical and Radiobiological Benefits," Reviews of Modern Physics, vol. 82(1):383-425 (Mar. 2010).
Schlosser J., et al., "Radiolucent 4D Ultrasound Imaging: System Design and Application to Radiotherapy Guidance," IEEE Transactions on Medical Imaging, Oct. 2016, vol. 35, No. 10, pp. 2292-2300.
Shackleford J.A., et al., "On Developing B-Spline Registration Algorithms for Multi-Core Processors," Phys. Med. Biol., vol. 55, pp. 6329-6351 (Oct. 2010).
Sharma A., et al., "New Non-Invasive Therapy for Cardiac Arrhythmias using Stereotactic Radiosurgery: Initial Feasibility Testing," Heart Rythm, vol. 4(5):S68, Abstract (May 2007).
Sharma A., et al., "Non-Invasive Ablation of the Left Superior Pulmonary Vein-Left Atrial Junction Using Stereotactic Focused Radiation," Circulation, vol. 116:489, Abstract (Oct. 2007).
Sharma A., et al., "Non-Invasive Approach to Myocardial Ablation: Pathology of Stereotactic Robot Targeted High Energy X-Ray Lesions at Potential Arrhythmia Sites," Heart Rhythm, vol. 5(5): S67 (AB32-3), Abstract (May 2008).
Sharma A., et al., "Noninvasive Stereotactic Radiosurgery (CyberHeart) for Creation of Ablation Lesions in the Atrium," Heart Rhythm, 2010, vol. 7, pp. 802-810, DOI: 10.1016/j.hrthm.2010.02.010.
Smith, Scott, Ultrasound Miniaturization, 2011 Joint AAPM / COMP Meeting Jul. 31-Aug. 4, 2011, Vancouver, available at: https://www.aapm.org/meetings/amos2/pdf/59-17269-42515-909.pdf.
Soejima K., et al., "Catheter Ablation in Patients With Multiple and Unstable Ventricular Tachycardias after Myocardial Infarction: Short Ablation Lines Guided by Reentry Circuit Isthmuses and Sinus Rhythm Mapping," Circulation, 2001, vol. 104, pp. 664-669.
Soejima K., et al., "Endocardial and Epicardial Radiofrequency Ablation of Ventricular Tachycardia Associated With Dilated Cardiomyopathy: The Importance of Low-Voltage Scars," Journal of American College of Cardiology, 2004, vol. 43, pp. 1834-1842, DOI: 10.1016/j.acc.2004.01.029.
Solevi P., "Study of an In-Beam PET System for CNAO, the National Centre for Oncological Hadrontherapy," PhD Thesis, Milano University, 2007, pp. 1-142 (144 Pages).
Sosnovik D.E., et al., "Magnetic Nanoparticles for MR Imaging: Agents, Techniques and Cardiovascular Applications," Basic Research in Cardiology, 2008, vol. 103, No. 2, pp. 122-130.
Suleiman M., et al., "The Noncoronary Cusp as a Site for Successful Ablation of Accessory Pathways: Electrogram Characteristics in Three Cases," Journal of Cardiovascular Electrophysiology, 2010.
Takami M., et al., "Effect of Left Atrial Ablation Process and Strategy on Microemboli Formation During Irrigated Radiofrequency Catheter Ablation in an In Vivo Model," Circulation. Arrythmia and Electrophysiology, 2016, vol. 9:e003226, DOI: 10.1161/CIRCEP.115.003226.
Topolnjak, et al., "Image-Guided Radiotherapy for Left-sided Breast Cancer Patients: Geometrical Uncertainty of the Heart," International Journal of Radiation Oncology, Biology, Physics, 82(4):e647-e655 (Mar. 2012).

(56) References Cited

OTHER PUBLICATIONS

Uhl M., et al., "High Control Rate in Patients With Chondrosarcoma of the Skull Base After Carbon Ion Therapy: First Report of Long-Term Results," Cancer, 2014, vol. 120, pp. 1579-1585.

Van Der Ree, et al., "Cardiac Radioablation—A Systematic Review," Heart Rhythm, vol. 17(8):1381-1392 (Aug. 2020).

Watts D.A., "Detectors for Quality Assurance in Hadrontherapy," Doctoral Thesis, University of Barcelona, May 30, 2013, 265 Pages.

Wellenberg R.H.H., et al., "Metal Artifact Reduction Techniques in Musculoskeletal CT-Imaging," European Journal of Radiology, 2018, vol. 107, pp. 60-69.

Yu L., et al., "Autonomic Denervation With Magnetic Nanoparticles," Circulation, 2010, vol. 122, pp. 2653-2659.

Zei P.C., et al., "Ablative Radiotherapy as a Noninvasive Alternative to Catheter Ablation for Cardiac Arrhythmias," Current Cardiology Reports, Published Online on Jul. 27, 2017, Nov. 1, 2018, vol. 19, No. 79, pp. 1-9, XP036310567, Retrieved from URL: https://www.ncbi.nlm.nih.gov/pmc/articles/PMC5532420.

\* cited by examiner

CARDIAC PHASE GATING SYSTEM FOR RADIATION THERAPY

RELATED APPLICATIONS

The present patent application is a National Phase entry of PCT Application No. PCT/IB2020/000930, filed Nov. 11, 2020, which claims the benefit of U.S. Provisional Patent Application No. 62/935,279, filed Nov. 14, 2019, and of U.S. Provisional Patent Application No. 63/028,053, filed May 21, 2020, the disclosures of which are hereby incorporated by reference in their entirety.

FIELD OF THE DISCLOSURE

This disclosure is directed generally to devices and techniques for particle irradiation therapy, and more specifically to non-invasive treatment of cardiac arrhythmias.

BACKGROUND OF THE DISCLOSURE

Cardiac arrhythmias are disruptions in the normal heartbeat. They affect more than two percent of the general population in Europe and are expected to at least double in the next 50 years as the population ages. Their occurrence is strongly linked to an increased risk of heart attacks and strokes.

More particularly, heart arrhythmia is a problem with the rate or rhythm of the heartbeat. The heart beats too quickly, too slowly, or with an irregular pattern. When at rest, the heart beating faster than normal, above 100 beats per minute in adults, is called tachycardia. The heart beating too slowly, below 60 beats per minute, is called bradycardia. A common type of arrhythmia is atrial fibrillation, which causes an irregular and fast heartbeat. Many factors can affect the rhythm of the heart such as having had a heart attack, smoking, congenital heart defects, and stress. Some substances or medicines may also cause arrhythmias.

Treatments may include medications, medical procedures such as ablation therapy or implantation of a pacemaker or defibrillator, and surgery. Medications for a fast heart rate may include beta-blockers or agents that attempt to restore a normal heart rhythm such as procainamide. Medications may have more significant side effects especially if taken for a long period of time. Pacemakers are often used for slow heart rates. Those with an irregular heartbeat are often treated with blood thinners to reduce the risk of complications. Those who have severe symptoms from an arrhythmia may receive urgent treatment with a controlled electric shock in the form of cardioversion or defibrillation.

Ablation therapies are often used to treat arrhythmias. Ablation therapies include burning or freezing specific heart tissues with invasive tools such as catheters, to stop the conduction of the disrupted electrical signals in these specific tissues. Invasive catheter ablation procedures are surgical interventions performed manually and the treatment efficacy varies largely from 50% to 80% depending on the technology used and skill of the surgeon. Moreover, the procedures can involve several medical staff members and can require many hours, during which patients are at risk of serious complications like tissue perforation, vein stenosis, or creation of a blood clot. The nature of the lesions created by catheter ablation results in procedures which are often repeated successive times, with increasing complexity for the medical staff and risk for the patient.

There is therefore a need for a non-invasive device and a non-invasive method of treatment of cardiac arrhythmias via non-invasive ablation based on charged particle beams, which can take into account the body motion in real time to provide a safe and effective treatment.

SUMMARY OF THE DISCLOSURE

Various embodiments of the disclosure relate to systems and techniques for reliably predicting a motion phase for enabling a particle beam (e.g., photons, electrons, carbon ions, protons, heavy ions) to irradiate a targeted tissue for non-invasive treatment of the heart. The disclosed system and methods utilize live two-dimensional (2D) or three-dimensional (3D) image streams (e.g., sequence of images in time, such as live ultrasound, live x-ray, MRI, or electrocardiographic imaging (ECGI) streams) of the heart. These image streams are herein referred to as 2D+time imaging and 3D+time imaging, respectively. The 2D+time and 3D+time imaging is used to identify the phase of the cardiac cycle and use this phase information to prospectively predict the cardiac motion in the future part of the cardiac cycle, thereby interpreting the real time (RT)-images of their respective image streams as relative time measurements. Accordingly, the live image stream effectively serves as time marker of the cardiac cycle for the prospective prediction.

The system and techniques do not require a defined regular number of input signals. Indeed, imaging systems (and ultrasound systems in particular) often operate at irregular acquisition time intervals. In some embodiments, the system is configured to discard any cardiac phase estimate that is considered too inaccurate for processing. In some embodiments, the motion phase predicted by the disclosed system is reliably generated even where the imaging does not provide real-time images at uniform time intervals. In some embodiments, spatial motion due to respiration as detected by optical markers on the imaging probe is monitored to provide a respiratory motion phase. In some embodiments, the system and methods account for both respiratory and cardiac cycles in characterizing the motion of the heart relative to the irradiation source.

In some embodiments, the system also includes a heartbeat sensor that provides an independent reference indication of the cardiac phase. The heartbeat sensor provides real-time or near real-time quality assurance of a current predicted phase indication. An example of a heartbeat sensor is an electrocardiogram, or ECG. An ECG monitors the electrical signals associated with the electrical activity of the heart and presents a characteristic R-wave peak. The R-wave peak provides one independent reference indication per cardiac cycle. While the ECG is frequently used throughout this disclosure as the heartbeat sensor, other heartbeat sensors are contemplated, including but not limited to acoustic sensors and blood pressure sensors.

The disclosed system may take into consideration some or all of the following: (a) the cardiac phase as determined by the most recent acquired real-time image(s); (b) optionally, the time of the last heartbeat sensor trigger pulse, corresponding to the beginning of a new cardiac cycle; (c) the time latency between the real-time image acquisition and the cardiac phase identification due to the time required to acquire and process the real-time image; and (d) the time latency needed to effectively switch the therapeutic beam on/off following a gating signal when in a beam-gating mode, or the time latency needed to effectively change beam parameters following a change of motion phase when in a beam-tracking mode. Processing of information (a) through (d) is initiated whenever a new real-time image or heartbeat sensor trigger pulse is acquired, and continuously updated and extrapolated to predict the cardiac phase at a time subsequent to the time of the most recent data acquisition.

In some embodiments, the disclosed system can be used in one of two modes: "beam-gating" and "beam-tracking". For beam-gating, the predicted cardiac phase is compared to the desired gating window, based on a patient-specific treatment plan, to determine if a gate ON or gate OFF signal should be set. For beam-tracking, the beam parameters (position, size, intensity, energy, among others) are dynamically adapted to a monitored motion of a target by sending the a predicted cardiac phase to a beam controller which loads an appropriate set of beam parameters (if not already loaded) for the actual motion state (as prescribed by the treatment plan for this motion state) based on the patient-specific and motion phase-dependent treatment plans.

Historically, cardiac cycles have been characterized with an ECG signal 30, depicted in FIG. 1. However, for non-invasive treatment of cardiac arrhythmias with particle beams, where accurate predictions of cardiac motion and cardiac tissue position is required, the ECG is inadequate. Consider that the ECG can reliably send only one data point per cardiac cycle 32 (i.e., at an R-peak 34 of the ECG signal). As is often the case with cardiac arrhythmia patients, the period of the cardiac cycle can suddenly change from one heartbeat to the next one. Clinical data show that the period length can change by, for example, a factor two from one heartbeat to the next, as depicted at FIG. 1. For this reason, an ECG monitor will typically incorrectly estimate cardiac phases for irregular heartbeats, which are ubiquitous for patients having cardiac arrhythmias. In addition, the most suitable treatment time would most realistically be placed during the heart diastole, when heart motion is most slow and smooth. However, the signal from the T-wave (which correlates with the start of diastole) is typically small, round and very patient- and heart pathology-dependent, such that the real-time identification of diastole via, for example, electronic fast edge detection using the ECG signal is at least tenuous and impractical, perhaps impossible. As such, ECG gating does not provide real-time information on cardiac motion with the time resolution required for accurate prediction of the targeted tissue motion.

Furthermore, an ECG monitors only electrical signals of the heart, which especially for cardiac arrhythmia patients, are poorly correlated to the resulting mechanical motion of the heart. Consider the scenario of an ECG signal 40 that includes extra-systoles 42, as depicted in FIG. 2. While the extra-systoles 42 are in this case not detected by the R-wave trigger detection, the extra-systoles 42 nevertheless distort the regular mechanical motion of the heart. This potentially results in the treatment target assuming a different position or orientation than expected, which can lead to ineffective treatment of the target and potential damage to healthy tissue surrounding the target.

Charged particle beams are presently used for the treatment of tumors, which occurs in 20-30 sessions in separate days. These charged particle beams have the physical characteristic of depositing most of their energy in the last few millimeters of their path (so-called Bragg peak). By adjusting the transverse position and energy of the beam, any target volume can be precisely covered, sparing surrounding healthy tissues.

Exploratory research has ensued regarding how to provide a heart tissue ablating device and method comprising emitting beams of charged particles (mainly protons but also carbon, oxygen, and helium ions) for ablating the said heart tissue. However, since the position of the Bragg peak depends on the density of the body tissues traversed, any motion due to the physiological (inner) movements of the patient, such as respiration, heartbeat, digestion or other can result in a difference of density encountered by the incoming charged particle beam and therefore a different position of the Bragg peak. The precision of ablation with charged particle beams is therefore strongly sensitive to motion of the target and of the surrounding tissues that the treatment beam will encounter on its path to the target. This is one of the reasons why current charged particle beam treatments are mostly limited to the head, the neck, the hip region and more rarely, the trunk (pancreas, liver, and lung).

More recently, systems and methods for treating cardiac arrhythmias non-invasively using external particle beams have been developed where tracking of the heart motion is performed using real-time 3D+time imaging. See, e.g., International Publication Number WO 2019/096943 to Garonna, et. al. ("Garonna") owned by the owner of the current application, the disclosure of which is hereby incorporated by reference herein in its entirety except for express definitions and patent claims contained therein. In order to use real-time 3D+time imaging for motion characterization in three-dimensional space and time (so-called "4D"), the tissues imaged must be correlated, in both space and time, with the same tissues imaged using the reference off-line 3D+time system, used for treatment planning. Such off-line 3D+time systems include 4D computed tomography ("4D-CT"), such as the Siemens SOMATOM FORCE®, and magnetic resonance imaging (MRI) systems. The most direct approach to accomplish this is by the simultaneous acquisition of the real-time image streams and off-line imaging data.

However, simultaneous acquisition of real-time imaging and off-line data includes technical challenges. Consider that the presence of the metal components of the real-time imaging probe in the beam path of the off-line imaging scanner results in artifacts on the images of the off-line imaging scanner ("off-line images"), resulting in a deterioration of the final off-line image quality that directly affects the quality of the treatment plan that can be made based on the off-line images. Consider also that the imaging probe must be positioned by a technologist skilled in interpreting real-time images, such as a cardiologist, sonographer, or certified radiologist, who needs to interpret the live real-time images and confirm whether the correct anatomical structures are visualized with sufficient image quality. Such a technologist must be present at both the simulation stage (i.e., during off-line data acquisition) and at the treatment stage. Often, standard radiation therapy centers do not staff such skilled technologists.

A technical consideration for an ultrasound system is that the speed of sound of the tissues that the ultrasound waves travel through is assumed to be constant (1540 m/s), regardless of the medium. Because the various body tissues in the imaging path can have significantly different speed of sound coefficients, the constant speed assumption can cause so-called "speed of sound aberrations," by which a given anatomical structure appears to be located closer or further away from the ultrasound probe than in actuality. If these ultrasound images are then co-registered to off-line images, a misalignment of the anatomical structures may result.

Various embodiments of the disclosure utilize a regime that uses real-time imaging to infer the three-dimensional orientation of the target in real-time, without need for direct correlation of real-time imaging and off-line data. Instead, correlation between the off-line images and the real-time imaging during treatment stages utilizes the modeling of bodily motion cycles as a succession of motion phases.

In some embodiments, the technical solution is based on modeling the heart motion as the superposition of two distinct periodic motion patterns: respiratory motion and cardiac motion. The cycles of each of these motion patterns can be subdivided into successive discrete bins. In the case of respiratory motion, a cycle can be determined by the motion of the thorax or flux of air intake. In the case of cardiac motion, a cycle may be determined by the duration between two consecutive R-wave peaks in the cardiac cycle. The bins may be uniformly divided in time along their respective cycle so that each bin represents a fixed segment of the respective motion phase.

In some embodiments, the motion phase information is provided to the ablation therapy system for modification of treatment parameters, such as beam position/size/energy according to the treatment plan corresponding to this motion bin (beam-tracking) or such as beam interruption (beam-gating). By avoiding simultaneous acquisition of real-time imaging and off-line data, there are no artifacts on the off-line images due to the presence of the imaging probe, a radiologist or sonographer need be present only once per patient at the treatment phase, and no co-registration is needed between the images at the simulation and the treatment stages.

To facilitate this regime, which is the subject of this disclosure, a system is used to monitor both the cardiac motion (heartbeat) and respiratory motion in parallel, and to enable/disable (i.e., beam-gating: to selectively "gate" the beam) the therapy particle beam accordingly, or to change beam parameters according to the motion phase (i.e., beam-tracking). The system and techniques herein disclosed ensure a consistent and robust beam-gating/tracking mechanism irrespective of the motion sensor type (ultrasound, ECG, optical, or other) and irrespective of the frequency and regularity of the motion sensor. And, in contrast to using only the ECG signal to predict the cardiac motion phase, the real-time imaging enable the detection of multiple motion phases during the cardiac cycle. In addition, the real-time images enable monitoring of the actual mechanical motion of the heart, instead of just electrical signals therefrom, thereby enabling a more precise beam-gating or beam-tracking.

Furthermore, in some embodiments, a quasi-realtime quality assurance method is disclosed for determining how accurate the real-time imaging-based cardiac phase identification was for the immediately preceeding cardiac cycle. The quality assurance is provided by using a heartbeat sensor acquired simultaneously with the real-time imaging to precisely measure the time duration of the previous cardiac cycle, from which the precise occurrence in time of the cardiac phases can be inferred.

Motion binning is already used in medical imaging, for example, to reconstruct a 4D-CT acquisition of the thorax. See, e.g., Dieterich, et al., "Respiratory Motion Management for External Beam Radiotherapy", Practical Radiation Oncology Physics, Chapter 19, pp. 252-263, Elsevier Inc., 2016 (available at https://www.sciencedirect.com/science/article/pii/B9780323262095000195, last visited Nov. 10, 2020).

Structurally, a treatment system is disclosed including an accelerator and beamline, which create the required beam with given properties (intensity, position, angle and/or energy). A control system controls the accelerator and beamline for timely creation and delivery of the beam with desired properties. A patient position imaging system (based on, for example, double X-rays or Cone-beam Computed Tomography (CBCT)) verifies the patient positioning relative to the beam. In some embodiments, patient positioning is accomplished with a system including a robotic apparatus upon which the patient is immobilized.

Animal studies have demonstrated that charged particle beams can be used to ablate heart tissue. However, to ensure a safe, effective, and fast procedure, the disclosed system is able to monitor in real-time the motion of the patient inner tissues, to infer the motion of the treatment target and to adapt in consequence the beam delivery based on a pre-established treatment plan. The treatment plan provides information regarding the beam properties for one or more allowed motion phases. The motion phases may correspond to a combination of phases of the respiratory and cardiac cycles. This can involve beam-gating the beam when the motion phase is not within the allowed motion phases of the treatment plan, and beam-tracking, i.e., adapting the beam transverse and longitudinal characteristics based on the identified motion phase as prescribed by the treatment plan for this motion phase.

The system includes hardware and software structures. The imaging is performed fully non-invasively. That is, the system does not require fiducial markers to be implanted in the patient, and does not require insertion of the imaging system inside body cavities. In this regard, embodiments are disclosed where one or more real-time imaging systems are placed externally on the patient body in order to image the heart region from the abdominal or thoracic viewing windows. Imaging can be performed using one or more linear arrays, phased arrays, multi-plane (phased) arrays (also called T-shaped or X-plane), mechanically swept probes and matrix array imaging probes to acquire 2D or 3D images at frame rates that are faster than the cardiac cycle. The imaging devices may be used to simultaneously image parts of the heart. In some embodiments, by knowing the position of each imaging system inside the treatment room (using, for example, optical markers on each imaging device and optical cameras, or electromagnetic sensors), one can relate the position in space of an image with that of the other images. In some embodiments, the imaging devices are coupled with respiratory and cardiac motion sensors for determining the phase of the motion of the target.

In some embodiments, treatment planning relies on performing 3D+time system scans, possibly in combination with respiratory and cardiac sensors. Objectives of the planning include determining an ablation target for one or more phases of respiratory and cardiac cycles and the required beam properties (angle, energy, position, intensity) to effectively ablate the target while sparing sensitive surrounding healthy tissues during each of these motion phases or combination of these motion phases. In the case of beam-gating, the treatment plan includes information on all motion phases for which treatment is allowed, by defining a "gating window," a condition in which all motion under consideration are in phases that allow safe treatment.

In the case of beam-tracking, multiple treatment plans are created, each treatment plan being applicable for only a subset of all the motion phases, such that for each combination of motion phases, there is only one applicable treatment plan.

Various embodiments of the disclosure include a cardiac motion subsystem that provides a novel and effective method for monitoring and characterizing the cardiac motion. The purpose of the cardiac motion subsystem is to provide a cardiac phase to the radiation therapy control system that either enables or disables particle beam generation depending on the combination of the respiratory and cardiac phases (beam-gating) or loads the appropriate beam properties (treatment plan) corresponding to that combination of respiratory and cardiac phase (beam-tracking). In some embodiments, the cardiac motion subsystem generates a cardiac gating signal while a separate respiratory gating signal is provided by a separate device. The cardiac gating signal enables the treatment beam to irradiate the target when the heart is in a predefined cardiac motion phase. The cardiac motion is inferred from the real-time imaging of the heart using software that estimates the cardiac phase. The cardiac phase software provides a predicted current cardiac phase based on the most recently acquired real-time images and known latencies of the device, and outputs either a gating signal based on the personalized treatment plan (beam-gating) or the predicted cardiac phase for potentially adapting the beam characteristics (beam-tracking).

In some embodiments, the real-time imaging of the cardiac motion is acquired with an imaging probe placed on the patient thorax, such that its position on the thorax is stable irrespective of patient movements and such that constant pressure can be applied by the probe on the skin for proper imaging throughout the respiration cycle. Such a holder is available commercially, for example, the PROBEFIX, available from Usono (Netherlands) for cardiac ultrasound probes. See https://www.usono.com/probefix/, last visited Nov. 10, 2020. The real-time imaging provides a better method for monitoring the cardiac motion than does a cardiac electrical signal alone, because the ECG signal is reliable for only one trigger or reference point per cardiac cycle (the R-peak marking the start of cardiac systole), whereas the real-time imaging can provide multiple references per cardiac cycle for better time resolution for the extrapolated prediction. The cardiac motion subsystem can thus compute an appropriate cardiac gating signal and overlay it with an independent respiration gating signal to determine when the therapy beam should be enabled to irradiate the target.

The disclosed device and the system are convenient for the patient because they consist of a non-invasive procedure lasting less than two hours without anesthesia, typically in a single or at most a few out-patient sessions. The deep ablation of both the inner and the outer cardiac muscle tissue results in continuous 3D volumes instead of the ablation points or lines performed by conventional invasive ablation systems. The risk of infection due to surgery is eliminated. Also, unlike conventional radiotherapy for the treatment of tumors performed with X-ray, gamma-ray, or photon beams, there is no deposition of large doses of radiation to surrounding normal tissues.

The cardiac ablation system disclosed herein has been used with 2D+time ultrasound data from animals and humans with cardiac ultrasound probes for Trans-Thoracic Echocardiography (TTE) and Intra-Cardiac Echocardiography (ICE). Alternatively, the cardiac ablation system could be used with Transesophageal Echocardiography (TEE), with multiple non-coplanar 2D+time ultrasound images and with 3D+time ultrasound images, or with other imaging modalities (e.g., ultrasound elastography, computed tomography, magnetic resonance imaging, positron emission tomography, single-photon emission computerized tomography).

BRIEF DESCRIPTION OF THE DRAWINGS

Further particular advantages and features are apparent from the following non-limitative description of certain embodiments of the disclosure, which refer to the accompanying drawings.

DETAILED DESCRIPTION

Figure 1:
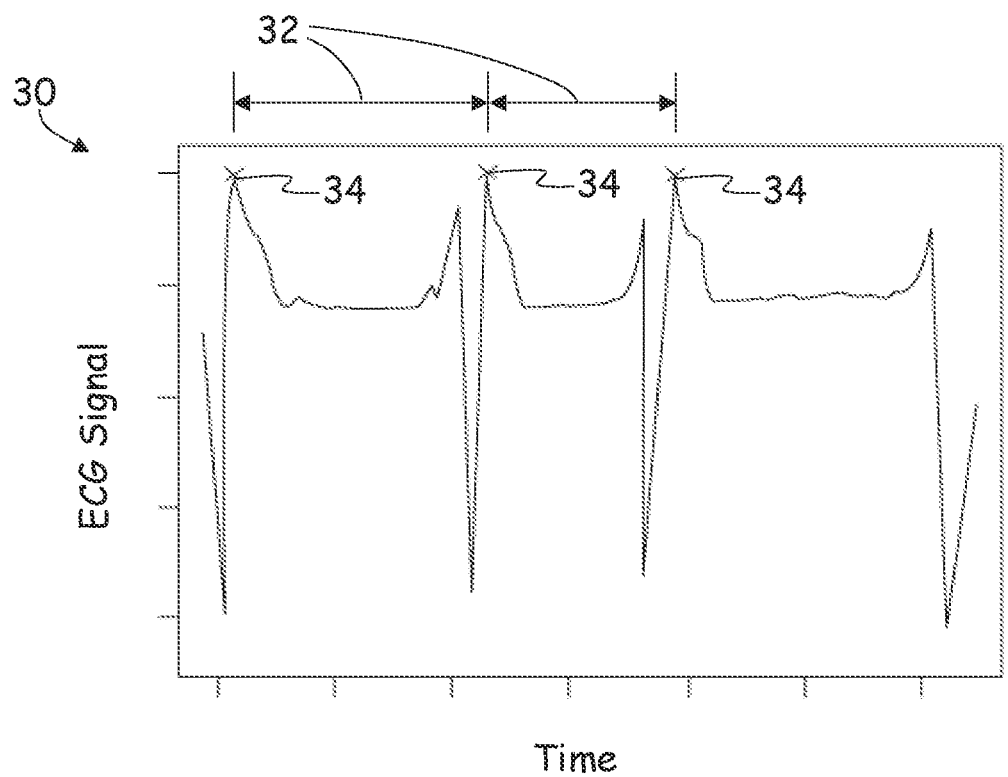
FIG. 1 is a plot of an electrocardiogram (ECG) signal depicting irregular cardiac cycles.
Figure 2:
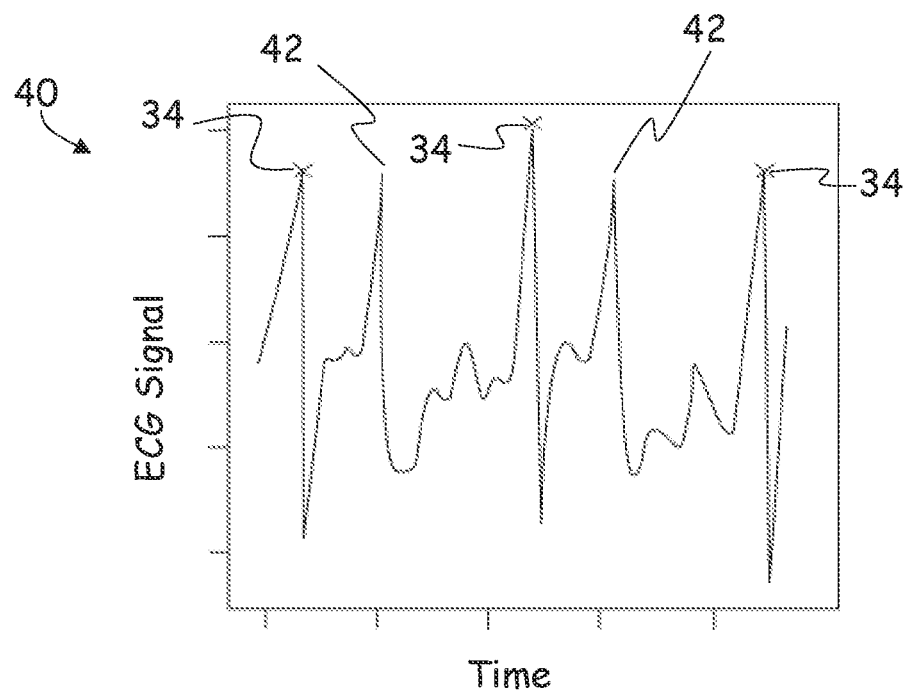
FIG. 2 is a plot of an ECG depicting electrical signals from irregular internal cardiac motion (extra-systoles)
Figure 3:
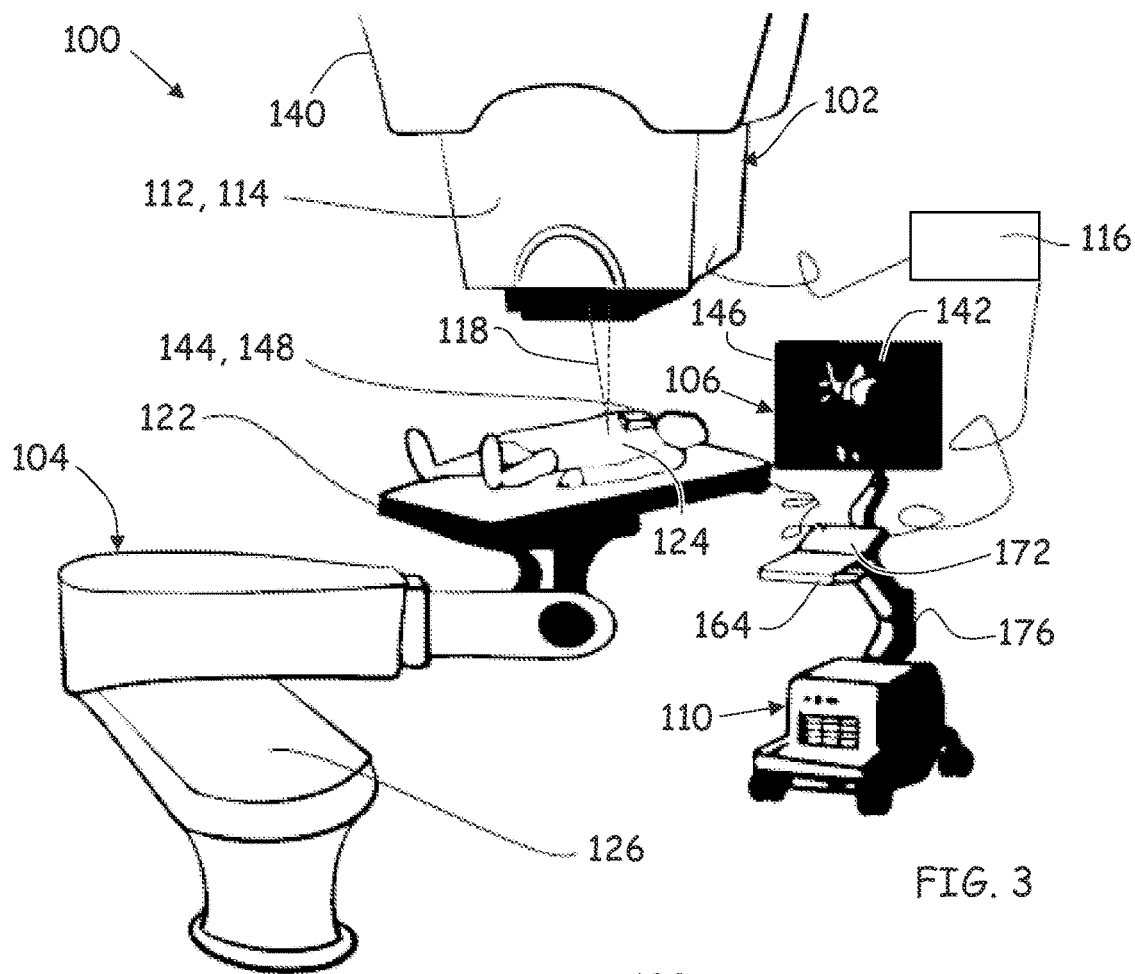
FIG. 3 is a perspective view of a cardiac ablation system according to an embodiment of the disclosure.
Figure 4:
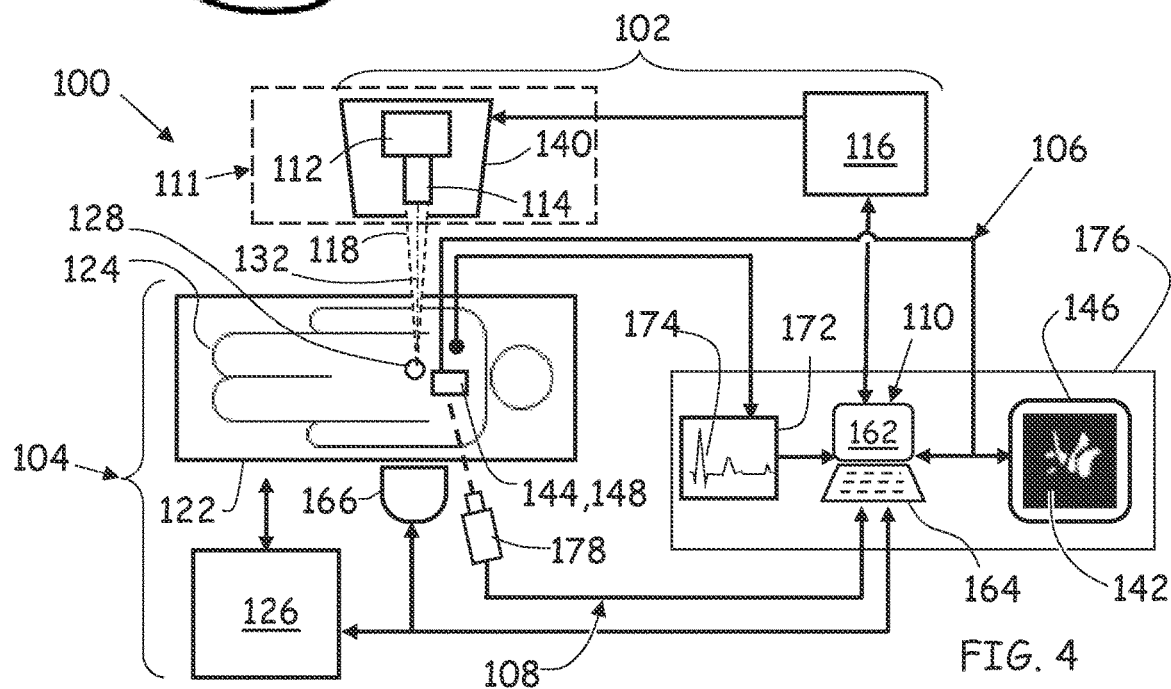
FIG. 4 is a schematic representation of the cardiac ablation system of FIG. 3 according to an embodiment of the disclosure.
Figure 5:
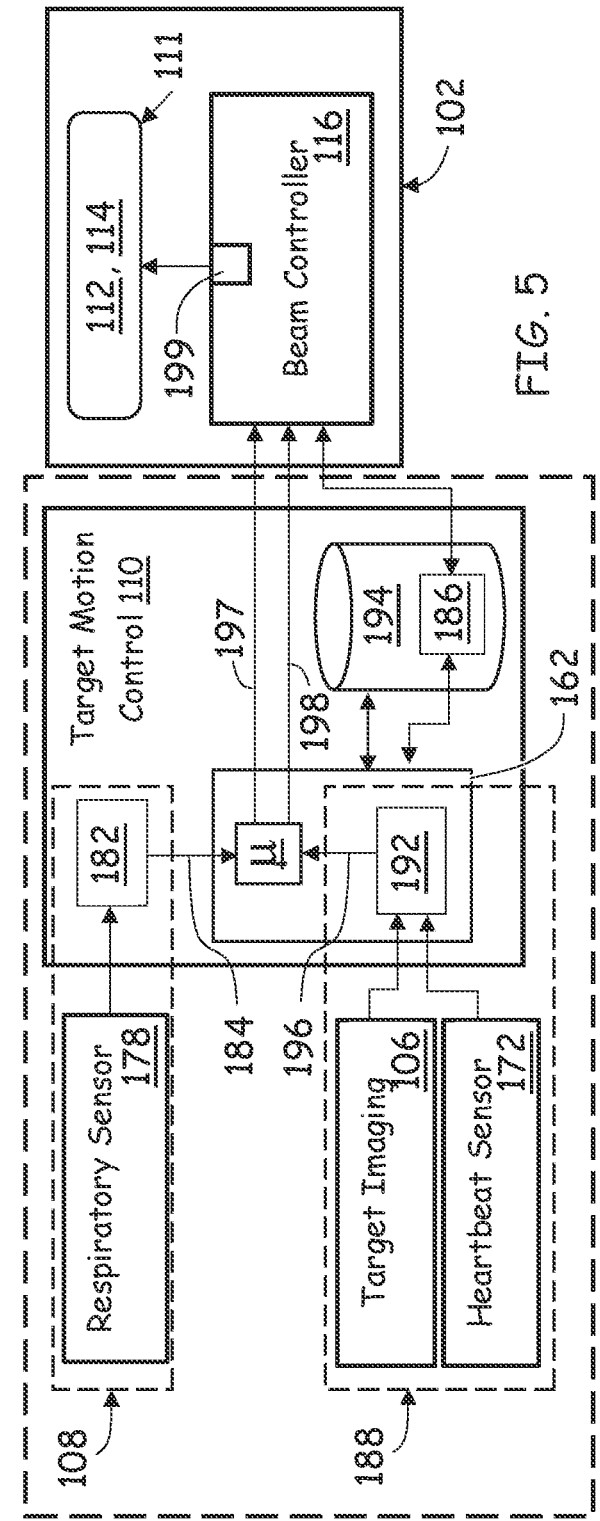
FIG. 5 is a block diagram depicting control of the cardiac ablation system of FIG. 3 according to an embodiment of the disclosure.

Referring to FIGS. 3 through 5, a non-invasive cardiac ablation system 100 is depicted according to an embodiment of the disclosure. The non-invasive cardiac ablation system 100 includes a charged particle emitting system 102, a patient positioning system 104, an online/real-time (RT) imaging system 106, an optional respiratory motion subsystem 108, and a target motion management system 110.

The charged particle emitting system 102 includes a particle emitter 111 and a beam controller 116 for selectively generating a particle beam 118. The particle emitter 111 may include an accelerator 112 and a beamline 114 operatively coupled to the beam controller 116. The patient positioning system 104 includes a patient support 122 and a positioner system 126. The patient support 122 is a device, such as a table or chair, upon which a patient 124 is positioned. The patient support 122 may include immobilization devices (not depicted) to help the patient 124 remain stationary during the ablation process. The positioner system 126 is for adjusting the position of a target region 128 within the patient 124 in a selected orientation in space (axial position, frontal position, median position, and the three respective rotation angles) relative to the treatment room coordinate system, to which the propagation axis 132 of the particle beam 118 is calibrated. The positioner system 126 may be robotized in order to hold a specific position and, on command, to perform translations and/or rotations of the patient 124 in space. Alternatively or in addition, components of the charged particle emitting system 102 (e.g., the beamline 114) may be mounted on a positioning system such as a robotic arm (not depicted) or a rotating mechanical frame or gantry 140 (depicted) to change the angle between the target region 128 and the propagation axis 132 to achieve the selected orientation imposed by the treatment plan.

The real-time imaging system 106 is coupled to the patient 124 and configured to provide real-time images 142 that either include resolution of the target region 128 or is used to infer the target region 128 position. The role of the real-time imaging system 106 is to acquire the real-time images 142 and send them to the target motion management system 110. In some embodiments, the real-time imaging system 106 includes at least one imaging probe 144 that is proximate the patient 124 for generation of real-time images 142 and may include a monitoring screen 146 for display of the real-time images 142. The imaging probe 144 may include any device (optical, electrical, magnetic, acoustic, among others) from which the present cardiac cycle phase can be identified. In some embodiments, such a device may include a simple time counter, which can determine in a predictive manner a current phase of the cardiac cycle based on established regular patterns for the specific patient and the most recently available cardiac phase information, as discussed below attendant to FIG. 11.

The imaging probe(s) 144 and/or probe holder 148 may include optical or magnetic markers so as to be able to localize and continuously monitor their position in the room coordinate system and to fuse or co-register their image to planning off-line images. Thus, the probe position in space can be measured and tracked in order to associate the registered localization markers with the anatomical structures in an off-line image. The real-time imaging system 106 may be configured to withstand some level of radiation exposure, such as indirect emission of neutrons and gamma rays from the incoming particle beam. Alternatively, some components of the real-time imaging system 106 (e.g., data processor) can be remote and signals transmitted via analog or digital data transmission cables. An example, non-limiting sampling rate for the real-time imaging system 106 is 10-30 Hz inclusive. Herein, a range that is said to be "inclusive" includes the end point values of the stated range.

In some embodiments depicted and described herein, the real-time imaging system 106 is an ultrasound cardiac imaging system, and the imaging probe 144 is an ultrasound probe mounted on the patient 124. Such depictions and descriptions are non-limiting. Other real-time imaging systems 106 are contemplated, for example x-rays, MRI, and ECGI. Ultrasound systems, when utilized, may include one or multiple 2D or 3D ultrasound transducers for continuous visualization of the heart trans-abdominally (through the diaphragm or the liver) or trans-thoracically (between the ribs). The real-time imaging system 106 may be non-parallel, placed in apical position or parasternal position, and/or image long-axis or short-axis heart structures affected by heart motion. Positioning and tuning of the devices may be made by an operator, but a probe holder 148 enables fixing the position for long continuous acquisition times (e.g., about 1 to 2 hours), with only remote supervision and control.

The target motion management system 110 includes hardware control and signal capabilities that are coupled to a central target motion controller 162. The target motion management system 110 may include a control console 164 for user interface with the central target motion controller 162. The central target motion controller 162 is operatively coupled to receive input from and/or send output to the charged particle emitting system 102, the patient positioning system 104, the real-time imaging system 106.

In some embodiments, the non-invasive cardiac ablation system 100 includes a patient position verification system 166 for verification of the patient positioning (FIG. 4). In some embodiments, the position verification system 166 ensures that the patient position in the room coordinate system is acceptably close to the patient position during simulation off-line data acquisition. The patient position verification system 166 may be, for example, a double X-ray or a cone-beam computed tomography (CBCT) imaging system. The position of the target region 128 may be inferred with the patient position verification system 166 from readily identified anatomical features (e.g. bone structures) that are near to and have a known spatial relationship with the target region 128. In some instances, features within the target region 128 itself may be identified directly with the patient position verification system 166, for enhanced accuracy in identifying the target region 128 relative to the particle beam 118. An example of a suitable patient position verification system 166 is the IMAGINGRING® System developed by medPhoton GmbH (Salzburg, Austria). The patient position verification system 166 may be coupled to the positioner system 126, the target motion management system 110, or both.

In some embodiments, the non-invasive cardiac ablation system 100 includes a heartbeat sensing system 172 that generates cardiac cycle data 174, such as an ECG measuring the electrical activity generated by the heart. The role of the heartbeat sensing system 172 is to acquire and send the cardiac cycle data 174 to the target motion management system 110. The non-invasive cardiac ablation system 100 may also include a respiratory monitor (not depicted). The heartbeat sensing system 172 and respiratory monitor may be coupled to the target motion management system 110. In some embodiments, the target motion management system 110 is located on a workstation 176. The workstation 176 may also house the monitoring screen 146 and the heartbeat sensing system 172.

The respiratory motion subsystem 108 includes a respiratory sensor 178 that monitors the respiratory motion of the patient 124. The respiratory sensor 178 may include any device (optical, electrical, magnetic, acoustic, among others) from which the present respiratory cycle phase may be inferred. In some embodiments, such a device may include a simple time counter, which in a predictive manner can determine the current phase of the respiratory cycle based on established regular patterns for the specific patient.

For example, the respiratory motion subsystem 108 may include optical markers placed on the imaging probe 144 or the probe holder 148 that is attached to the chest of the patient 124, and the optical markers are viewed with an optical camera (depicted). Optical cameras suitable for this purpose include include the FUSIONTRACK® 500 manufactured by Atracsys LLC (Puidoux, Switzerland). The respiratory motion subsystem 108 may also include surface tracking capabilities, for example using lasers or thermal imaging.

The respiratory motion subsystem 108 is coupled to the target motion management system 110. In some embodiments, the respiratory motion subsystem 108 may be a standalone system that includes a respiratory control module 182, the respiratory control module 182 being external to the central target motion controller 162 (depicted). In some embodiments, the respiratory control module 182 resides within the central target motion controller 162 (not depicted). The respiratory motion subsystem 108 may output a respiratory motion signal 184 or respiratory motion phase signal that is based on the phase of the respiratory cycle. Determining the status of the respiratory motion signal 184 is described attendant to FIG. 10 below.

A cardiac motion subsystem 188 is interfaced with the target motion management system 110 (FIG. 5). The cardiac motion subsystem 188 includes the real-time imaging system 106, the heartbeat sensing system 172, and a cardiac phase gating module 192. The cardiac phase gating module 192 may reside within the central target motion controller 162 (depicted). The target motion management system 110 imports and timestamps the data stream of real-time images 142, the cardiac cycle data 174, the R-wave trigger pulse 264 (FIG. 9), and, in some embodiments, stores the data on a tangible, non-transitory storage medium 194. The cardiac phase gating module 192 executes cardiac motion phase identification in real-time (discussed below attendant to FIG. 11) and manages external signal inputs and outputs. The output of the cardiac motion subsystem 188 is a cardiac motion signal or cardiac phase signal 196, which may be based on the phase of the cardiac cycle and prescribed by an ablation treatment plan 186. The ablation treatment plan may be stored on the storage medium 194 or accessed from elsewhere.

Figure 6:
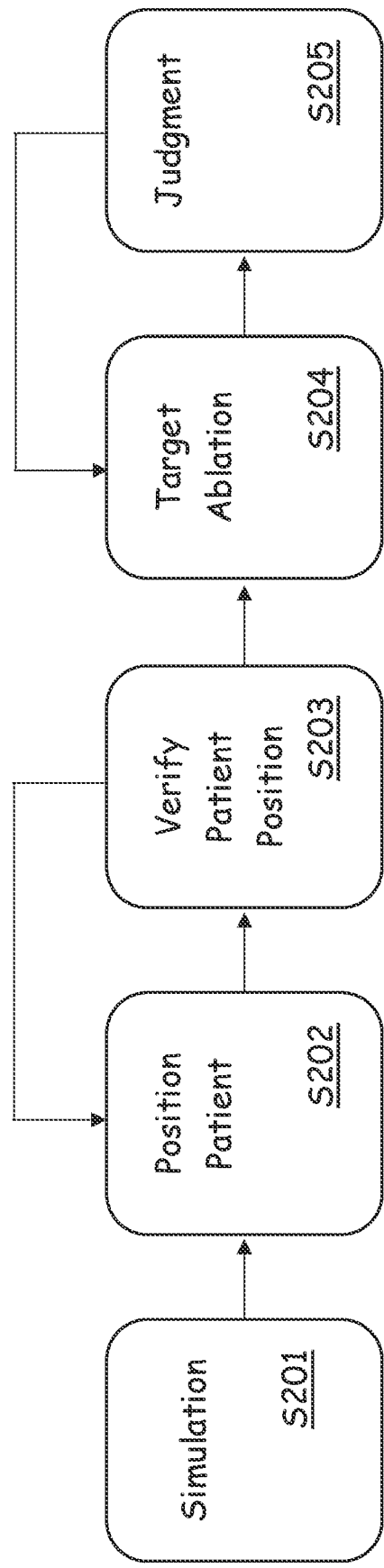
FIG. 6 schematically represents a cardiac treatment method according to an embodiment of the disclosure.

The ablation treatment plan 186 is a comprehensive plan that forms the basis of control, execution, and performance verification of the non-invasive cardiac ablation system 100 during the target ablation and judgment stages S204 and S205 (FIG. 6). The ablation treatment plan 186 includes a patient-specific list of treatment properties in order to irradiate the appropriate volume in the patient body with the required therapeutic radiation dose. The treatment properties may include treatment target volume, treatment target motion boundaries, motion landmark positions, personalized parameters for cardiac phase identification, personalized parameters for respiratory phase identification, beam species, irradiation angles, beam sizes, beam positions, beam energies, beam intensities, dose for each irradiation voxel and treatment field, patient position in room, applicable motion phases or gated motion phases, among others. A treatment plan is specific for a given set of motion phases (not excluding all motion phases). These properties are computed based on off-line image scans (static or time-resolved), where the medical staff has defined the clinical target which should receive a given dose, the margins around the clinical target that consider the possible errors related to patient positioning and motion during the delivery), the critical healthy tissues that should be irradiated in the least possible fashion and the gating windows within which irradiation is allowed (beam-gating) or motion phases for which the treatment plan applies (beam-tracking).

The ablation treatment plan 186 may include, but is not limited to, the following: contouring the target region in off-line images for one or more motion phases; determining the beam properties for each of the chosen motion phases based on the target region and surrounding healthy tissues; and determining, for each of the chosen motion phases, boundaries for the target region outside of which irradiation should be stopped because it is unsafe. The contouring step may be performed by medical staff. A given motion phase may combine various motion phases (e.g., respiratory and cardiac cycle phases). In some embodiments, the ablation treatment plan 186 involves defining a volume of the target region 128, defining the motion of the target region 128, prescribing a therapeutic dose and irradiation angle(s), and identifying critical tissues in the path of the particle beam 118 and their dose limits.

The ablation treatment plan 186 may also specify the gating of the charged particle emitting system 102 as a function of various motion phases in a process referred to herein as "binning." An example of the binning process for determining the status of the cardiac motion signal 196 is described attendant to FIG. 9 below. The gating window may also be adapted by the responsible clinical staff on treatment day based on experience and patient status (e.g., difficulty to hold the breath, faster respiration rate).

The target motion management system 110 outputs two signals to the beam controller 116: a gating signal 197 and a digital communication signal 198. In the beam-gating mode, the target motion management system 110 outputs the gating signal 197. In the beam-tracking mode, the target motion management system 110 outputs values via the digital communication signal 198 corresponding to the respiratory motion signal 184 and the cardiac motion signal 196. In some embodiments, the signals 184 and 196 represent the current predicted phases of the respective respiratory and cardiac cycles. For example, the signals 184 and 196 may each represent a value between zero and 0.999999 indicative of the current predicted fraction of the respective total cycle normalized to 1. The signals 184 and 196 are sent to a processor μ of the central target motion controller 162. Using the ablation treatment plan 186, the central target motion controller 162 determines the gating status of the combined signals 184 and 196 and sends the gating signal 197 to the beam controller 116. In some embodiments (beam-tracking), the central target motion controller 162 instead processes and relays the information about the respiratory and cardiac phases to the beam controller 116 via the digital communication signal 198.

Functionally, the charged particle emitting system 102 produces the particle beam 118 with the required properties for ablation of the target region 128. These properties include the intensity, convergence position, approach angle, and total energy of the particle beam 118. The beam controller 116 configures the required properties of the beam 118 from relevant aspects of the ablation treatment plan(s) 186, to which the beam controller 116 has access. The configuration of the beam 118 may be based on information received from the target motion management system 110 via the digital communication signal 198, such as the monitored motion of the target region 128 (current motion phase). The beam controller 116 may also set an on/off switch 199 to enable or to gate the charged particle emitting system 102 based on the gating signal 197 sent by the central target motion controller 162.

Herein, to "enable" the charged particle emitting system 102 is to cause the particle beam 118 to irradiate the patient 124, while to "gate" the system 102 is to prevent the particle beam 118 from irradiating the patient. More generally, the term "beam-gating" refers to sending a signal to the beam controller 116 to either pause the irradiation or resume the irradiation as planned. The way such enablement and gating is achieved is system specific. Some systems enable the particle beam 118 by activating the accelerator 112 and gate the particle beam 118 by deactivating the accelerator. Other systems leave the accelerator activated and gate the charged particle emitting system 102 by blocking or diverting the particle beam 118 so that the patient 124 is not irradiated.

The non-invasive cardiac ablation system 100 also delivers the particle beam 118 to the target region 128 at predetermined phases of certain bodily motion cycles. Such bodily motion cycles may include respiratory and cardiac cycles. The real-time imaging system 106 provides the real-time images 142 from the real-time imaging to the target motion management system 110. The target motion management system 110 utilizes the real-time images 142 to deliver the particle beam 118 at the predetermined respiratory and cardiac phases. The real-time images 142 may also be used to determine the properties required of the particle beam 118.

In some embodiments, the respiratory phase is sensed by measuring a spatial displacement of the abdominal region or thorax of the patient 124, such as the optical markers placed on the imaging probe 144 or probe holder 148 (discussed above). Examples of respiratory motion subsystems 108 include the VARIAN RPM, manufactured by Varian Medical Systems, Inc. (Palo Alto, California, U.S.A.) and the ANZAI BELT (AZ-733VI), manufactured by Anzai Medical Co., Ltd (Tokyo, Japan). Alternatively, the respiratory motion subsystem 108 could utilize images of the real-time imaging system 106 as a surrogate of respiratory motion by identifying an appropriate landmark in the image and following the motion of the landmark in the image along the respiratory cycle.

The real-time images 142 may be acquired and updated to the target motion management system 110 continuously, providing the operator with a live stream of data. The real-time images 142 and cardiac cycle data 174 may also be stored on a storage medium 194. The stored real-time images 142 can be later analyzed to assess the accuracy of the phase prediction process (described attendant to FIG. 11 below) and, if needed, to adapt the software parameters specific to the patient 124.

Figure 7:
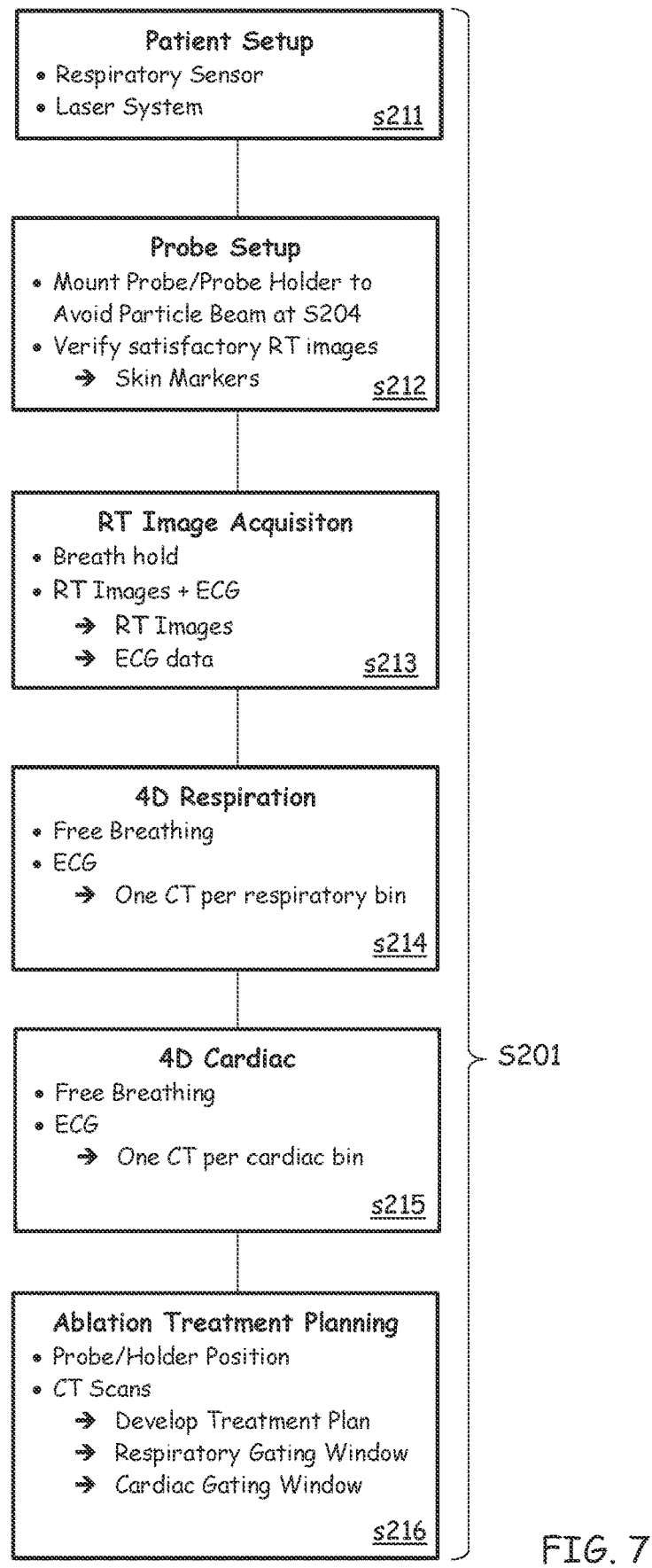
FIG. 7 is a flow chart of the simulation stage of FIG. 6 according to an embodiment of the disclosure.
Figure 8:
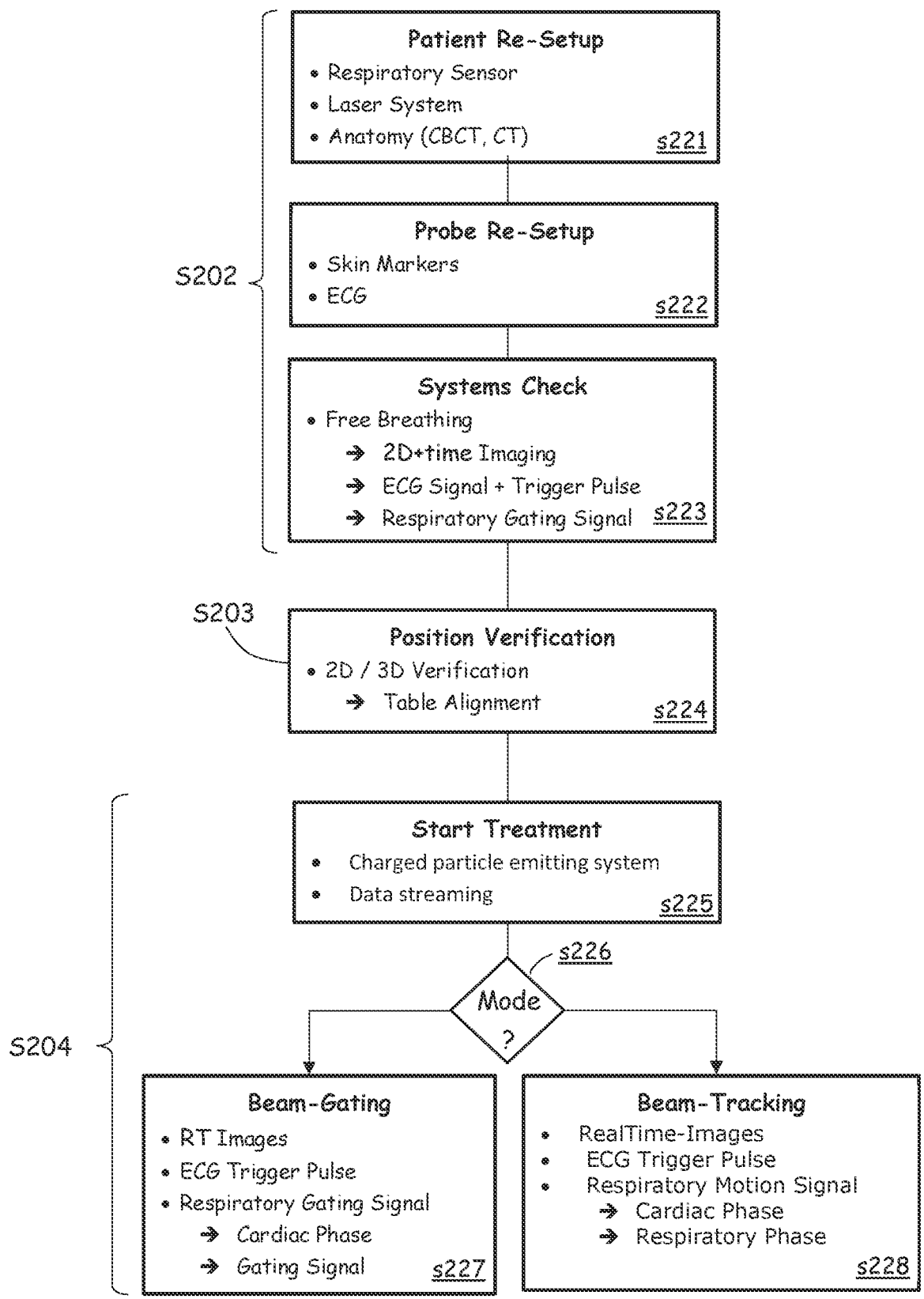
FIG. 8 is a flow chart of the patient positioning, verification, and target ablation stages of FIG. 6 according to an embodiment of the disclosure.

Referring to FIGS. 6 through 8, a workflow process 200 for planning and execution of the ablation therapy treatment is schematically depicted according to an embodiment of the disclosure. The general workflow process 200 includes a simulation stage S201, a patient positioning stage S202, a patient position verification stage S203, a target ablation stage S204, and a judgment stage S205.

The simulation stage S201 is depicted in greater detail at FIG. 7. The simulation stage S201 includes a patient setup step s211, a probe setup step s212, a real-time (RT) image acquisition step s213, acquisition of off-line data for respiration motion (step s214) and cardiac motion (step s215), and an ablation treatment planning step s216. For clarity of presentation, FIG. 7 depicts steps s213 through s215 as occurring successively. In some embodiments, two or more of steps s213 through s215 may be performed simultaneously.

The patient setup step s211 includes situating the patient 124 on the patient support 122 in the treatment room and coupling the respiratory motion subsystem 108 and the patient position verification system 166 to the patient 124.

The probe setup step s212 involves coupling of the real-time imaging system 106 to the patient 124. The imaging probe 144 and probe holder 148 are to be positioned in substantially the same manner during both the simulation stage S201 and the target ablation stage S204. Accordingly, during the simulation stage S201, consideration is given so that, during the target ablation stage S204, the imaging probe 144 and probe holder 148 does not encroach the path of the particle beam 118. The real-time images 142 may be initially monitored to facilitate adjustment of the imaging probe 144 and probe holder 148 for satisfactory real-time imagery. The position of the probe holder 148 may be marked with skin markers on the patient 124. The patient position may also be recorded, for example using the patient position verification system 166. The phase identification aspect of the cardiac gating module 192 may be used in the simulation stage S201 to customize algorithm parameters and optimize the performance for the specific patient.

For the real-time image acquisition step s213, data is acquired from the patient 124 simultaneously with the real-time imaging system 106 and the heartbeat sensing system 172. In some embodiments, the patient 124 is instructed to hold his or her breath over several cardiac cycles, so that the real-time images 142 are representative of cardiac motion only.

The off-line data for respiration motion step s214 is acquired to characterize the motion of the target region 128 that is induced by breathing of the patient 124. As such, the patient 124 may breathe freely during step s214. Alternatively, the patient may be instructed to hold breath in deep-inspiration or deep-expiration, or some forced ventilation system (jet ventilation among others) may be used to impose a respiratory cycle and motion that is known a priori. In some embodiments, the heartbeat sensing system 172 acquires cardiac cycle data 174 during step s214. The data stream of respiratory off-line data and corresponding cardiac cycle data 174 is stored for evaluation and incorporation into the ablation treatment plan 186. Also, if necessary, a probe check may be performed wherein the imaging probe 144 is replaced with a dummy plastic probe to avoid artifacts on the off-line images. In some embodiments, the quantity of respiratory off-line data acquired during step s214 is sufficient to resolve at least one 3D scan (e.g., CT scan) per designated respiratory bin 282, discussed attendant to FIG. 10 below.

The off-line data for cardiac motion step s215 is acquired to characterize the motion of the target region 128 that is induced by the cardiac cycle. In some embodiments, the patient 124 breathes freely during step s215. Alternatively, the patient may be instructed to hold the breath in deep-inspiration or deep-expiration or some forced ventilation system (jet ventilation among others) may be used to impose a respiratory cycle and motion that is known a priori. In some embodiments, the heartbeat sensing system 172 acquires cardiac cycle data 174 during step s215. The data stream of cardiac off-line data and corresponding cardiac cycle data 174 is stored for evaluation and incorporation into the ablation treatment plan 186. As in step s214, a probe check may be executed. In some embodiments, the quantity of cardiac off-line data acquired during step s215 is sufficient to resolve at least one 3D scan (e.g., CT scan) per designated cardiac phase bin 254, discussed attendant to FIG. 9 below.

The ablation treatment planning step s216 of the simulation stage S201 involves developing the ablation treatment plan 186, for example as described above. The simulation stage S201 may be performed for one or more respiratory and cardiac cycles. The target volume may range from approximately 2 to 200 cubic centimeters (cc) inclusive. In some embodiments, the therapeutic dose may vary or otherwise be in a range from approximately 20 to 60 Gray (Gy) inclusive.

Stages S202 through S205 are executed the day of treatment. The activity performed for stages S202 through S204 are presented in greater detail in FIG. 8. The patient positioning stage S202 may include a patient re-setup step s221, a probe re-setup step s222, and a systems check step s223.

For the patient re-setup step s221, the respiratory motion subsystem 108 and the patient position verification system 166 is coupled to the patient 124 and the patient 124 positioned on the patient support 122 in the same position as was done for the patient setup step s211 of the simulation stage S201. The patient 124 may be secured with immobilization devices. In addition, anatomical aspects of the positioning of the patient may be verified (e.g., with cone-beam computed tomography).

At the probe re-setup step s222, the imaging probe 144 and probe holder 148 may be remounted by using the skin markers established at step s212 of the simulation stage S201. The heartbeat sensing system 172 is also coupled to the patient 124.

A systems check step s223 is performed to make sure the real-time imaging system 106, heartbeat sensing system 172, and the respiratory motion subsystem 108 are operatively coupled to the target motion management system 110. The real-time images 142 may be monitored over a few cardiac cycles to facilitate fine adjustment of the imaging probe 144 and probe holder 148 and confirm that the real-time imagery is congruent with the real-time imagery of step s213 of the simulation stage S201. Once the real-time imagery is deemed appropriate, the real-time images 142 and corresponding cardiac cycle data 174 are streamed to the target motion management system 110 and may be analyzed by the software of the cardiac motion subsystem 188 in quasi-real time for at least a few cardiac cycles.

After completion of the patient positioning stage S202, the patient position verification stage S203 is carried out. At a position verification step s224, 3D position verification of the patient 124 relative to the propagation axis 132 of the particle beam 118. The 3D position verification may involve the placement of the patient 124 on the patient support 122, as well as manipulation of the patient support 122 with the positioner system 126. The patient positioning and verification stages S202 and S203 may be iteratively performed until the position of the patient 124 is the same as for the off-line imaging of the simulation stage S201, as determined by the patient position verification system 166. Also, for cases where the ablation treatment plan 186 calls for multiple angles, when irradiation is completed at one configuration of the gantry 140, irradiation is stopped and the beam controller 116 orients the gantry 140 to the new pre-determined angle. If necessary, the patient positioning and position verification stages S202 and S203 are repeated.

The target ablation stage S204 commences upon verification of satisfactory patient positioning. The target ablation stage S204 includes a start treatment step s225. The start treatment step s225 involves readying the non-invasive cardiac ablation system 100 for particle beam emission. Activities may include arming the charged particle emitting system 102, for example by powering up the accelerator 112, and starting the streaming of data from the respiratory and cardiac motion subsystems 108 and 188.

Depending on the mode of operation (s226), either a beam-gating step s227 or a beam-tracking step s228 is executed by the target motion management system 110. In the beam-gating mode, the target motion management system 110 executes step s227. The central target motion controller 162 may search for the position of the landmarks on the live real-time images 142 via manual, semi-automatic or automatic image segmentation and registration. Alternatively, the central target motion controller 162 may analyze the real-time images 142 to identify the current cardiac phase (and in some embodiments, the respiratory phase). Based on this information and, in some embodiments, also on the information from the respiratory sensor 178 and the heartbeat sensing system 172, the central target motion controller 162 may determine if cardiac and respiratory cycle phase are within the gating window and send the gating signal 197 (enable/disable) or motion phase information via the digital communication signal 198 to the beam controller 116. In the case of beam-tracking, the beam controller 116 loads the appropriate ablation treatment plan 186 corresponding to the current motion phase (if not already loaded) and configures the particle emitting system 102 accordingly (if not already correctly configured).

The beam-gating step s227 involves determining whether the anticipated position of the target region 128 relative to the particle beam 118 will be suitable should the particle emitting system 102 be enabled. If so, the particle emitting system 102 is enabled; if not, the particle emitting system 102 is disabled (gated). If enabled, the particle beam 118 is emitted by the particle emitting system 102 at a prescribed angle and directed to the prescribed target region 128 of the heart (as determined during treatment planning). During the target ablation stage S204, non-invasive imaging using the real-time imaging system 106 as well as cardiac cycle monitoring with the heartbeat sensing system 172 may also be acquired. The gating determination is based on the data stream of real-time images 142, trigger pulses 264, and the respiratory motion signal 184.

In some embodiments, from the real-time images 142, and possibly from the cardiac cycle data 174 and/or respiratory cycle monitoring data, the system recognizes the relevant motion phase of the off-line data and infers the relevant ablation treatment plan 186 for that motion phase. This can be achieved through image segmentation and registration on the real-time images 142 to determine the position of the fiducials (reference points/lines) on the real-time images 142.

In the beam-tracking mode, the motion control system 110 executes step s228. The beam-tracking step s228 involves determining whether the anticipated position of the target region 128 relative to the particle beam 118 will correspond to the beam parameters for the current treatment plan loaded by the particle emitting system 102. If so, the particle emitting system 102 is enabled; if not, the particle emitting system 102 modifies the appropriate beam parameters by loading the appropriate treatment plan before being enabled.

Similar to beam-gating, if enabled, the particle beam 118 is emitted by the particle emitting system 102 at a prescribed angle and directed to the prescribed target region 128 of the heart (as determined in the loaded treatment plan). Also similar to the beam-gating, during the target ablation stage S204, non-invasive imaging using the real-time imaging system 106 as well as cardiac cycle monitoring with the heartbeat sensing system 172 may also be acquired. The motion phase determination is based on the data stream of real-time images 142, trigger pulses 264, and the respiratory motion signal 184. In contrast to beam-gating, beam-tracking provides multiple treatment plans, and each motion phase (combination of cardiac and respiratory phase or phases) has its corresponding treatment plan and beam properties.

Figure 9:
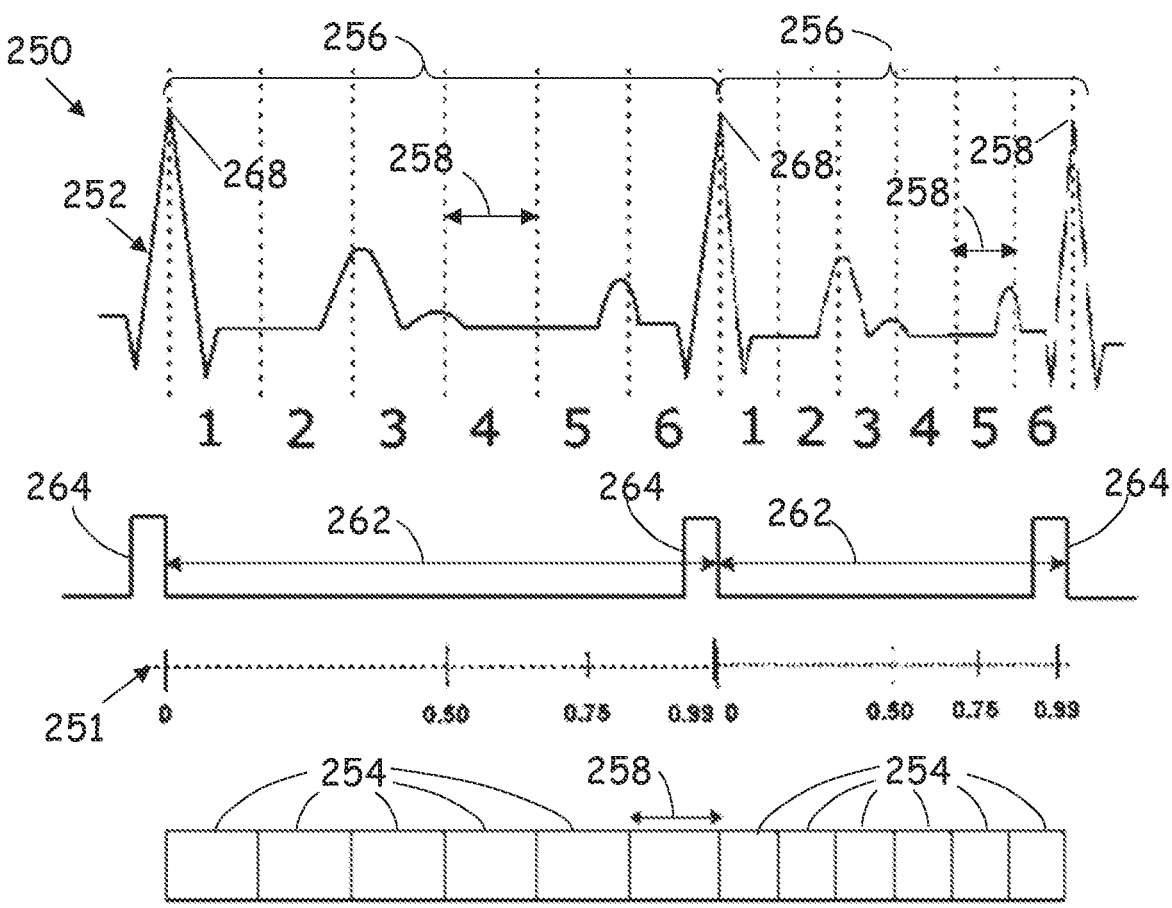
FIG. 9 is a time flow diagram of a cardiac binning process according to an embodiment of the disclosure.

Referring to FIG. 9, a time flow diagram of a cardiac binning process 250 is depicted according to an embodiment of the disclosure. The heartbeat sensing system 172 (FIG. 4) is used to independently measure a cardiac signal 252 indicative of cardiac phase 251. Herein, the cardiac phase 251 is a value that ranges from 0 to 0.999999 inclusive, representing a continuum from the beginning to the end (inclusive) of a cardiac cycle 256. For purposes of illustration, the cardiac signal 252 is depicted as being subdivided into six cardiac phase bins 254 per cardiac cycle 256 in FIG. 9. In some embodiments, 10-20 cardiac phase bins 254 are used to resolve the cardiac motion.

The cardiac phase bins 254 may be uniformly divided in time so that each cardiac phase bin 254 represents a time segment 258, each time segment 258 being equal to a time period 262 of the cardiac cycle 256 divided by the total number of cardiac phase bins 254. As such, for a given cardiac cycle 256, each cardiac phase bin 254 represents a fixed segment of the motion phase. Because the time period 262 of the cardiac cycles 256 can vary from heartbeat to heartbeat, as illustrated in FIG. 9, uniformly dividing each time period 262 of each cardiac cycle 256 among the total number of cardiac phase bins 254 effectively normalizes the binning so that a given cardiac phase bin 254 represents a fixed phase segment 266 of the cardiac phase 251 from cycle to cycle.

In some embodiments, the heartbeat sensing system 172 is an ECG monitor that includes three or more ECG electrodes placed on the thorax of the patient 124. Commercial ECG monitors can also output a trigger pulse 264 when an R-wave peak 268 is detected, also depicted in FIG. 9. In some embodiments, the trigger pulse 264 may be used to determine the exact time when a new cardiac cycle 256 starts. For this disclosure, the R-wave peak 268 of an ECG signal defines the beginning of the cardiac cycle 256. It is noted that this convention is non-limiting; that is, the beginning of a cardiac cycle 256 is arbitrary and may be defined anywhere along the cardiac cycle 256 as long as such arbitrary beginning of a cardiac cycle is established in a coherent fashion for both real-time and off-line imaging.

In some embodiments, the cardiac binning process 250 is performed retrospectively (i.e., after, not during, data acquisition) during the simulation stage S201. The retrospective treatment of the data enables accurate identification of the cardiac cycles 256 and better characterization of each cardiac phase bin 254 of the cardiac cycle 256. Cardiac cycle data, such as the trigger pulses 264, may also be used retrospectively during treatment, for example during the judgment stage S205, as a running check of the accuracy of the predictions of the cardiac phase 251.

Figure 10:
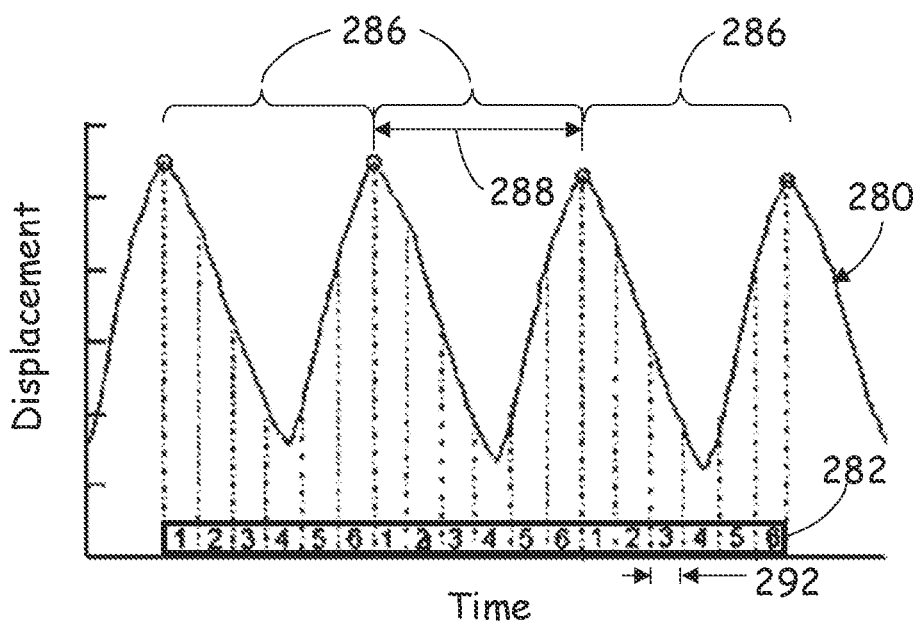
FIG. 10 illustrates binning of a respiratory signal according to an embodiment of the disclosure.

Referring to FIG. 10, an example illustration of binning for a respiratory motion signal 280 indicative of respiratory displacement motion is depicted according to an embodiment of the disclosure. The respiratory motion signal 280 is subdivided into six bins 282 per respiratory cycle 286 for the illustration. It is noted that the number of cardiac phase bins 254 for the cardiac cycle 256 of FIG. 9 does not have to equal the number of bins 282 for the respiratory cycle 286.

From the respiratory motion signal 280, a period 288 for each respiratory cycle 286 may be determined. Knowing the period 288, fixed phase segments 292 represented by each bin 282 of the respiratory cycle 286 can be determined. For each bin 282, a 3D scan of the thorax provides anatomical information about the patient 124 for that particular respiratory motion state and can be used for a treatment plan specific for the motion phases within this specific bin.

In some embodiments, the patient may be asked to sustain prolonged breath-holds, with the radiation treatment being performed during the prolonged breath-holds. Also, alternatively or in addition, a ventilator (not depicted) may be used in some embodiments to ensure that the respiration state is reproducible and constant during treatment. By applying radiation treatment only during the prolonged breath-holds or in synchronization with the ventilator, the need for independent monitoring and characterization of the respiratory cycle can be reduced or eliminated when determining the gating signal.

With the binning approaches of FIGS. 9 and 10, delivery of the particle beam 118 may be enabled when both the respiratory motion state and the cardiac motion state are within the designated treatment bins of the treatment plan 186 for the patient 124. The allowed treatment bins are defined during treatment planning based on 3D+time data (one scan per respiratory motion state and one scan per cardiac motion state).

Referring again to FIGS. 4, 5, and 9, other aspects of the cardiac phase gating module 192 are depicted according to embodiments of the disclosure. The cardiac phase gating module 192 utilizes the latest real-time image 142 streamed from the real-time imaging system 106 and outputs the estimated cardiac phase for that real-time image 142. Internally, the cardiac phase gating module 192 can store multiple images to obtain a sequence of the cardiac motion and estimates the cardiac phase 251 of the last real-time image 142 of the sequence. In some embodiments, the cardiac phase identification utilizes a deep neural network (i.e., artificial intelligence) such as the neural network 400 disclosed attendant to FIGS. 12-15. The deep neural network provides robust characterizations independent of the image acquisition parameters (e.g., contrast, orientation, quality), and the specifics of the patient heart cycle (e.g., change in cardiac cycle length, extra-systole indications, among others). The neural network 400 disclosed herein may be trained on large datasets of synchronized real-time images 142 and cardiac cycle data 174. In some embodiments, the cardiac cycle data 174 is retrospectively processed to determine the R-wave peaks and thus estimate a value of the cardiac phase 251 for each real-time image 142.

Figure 11:
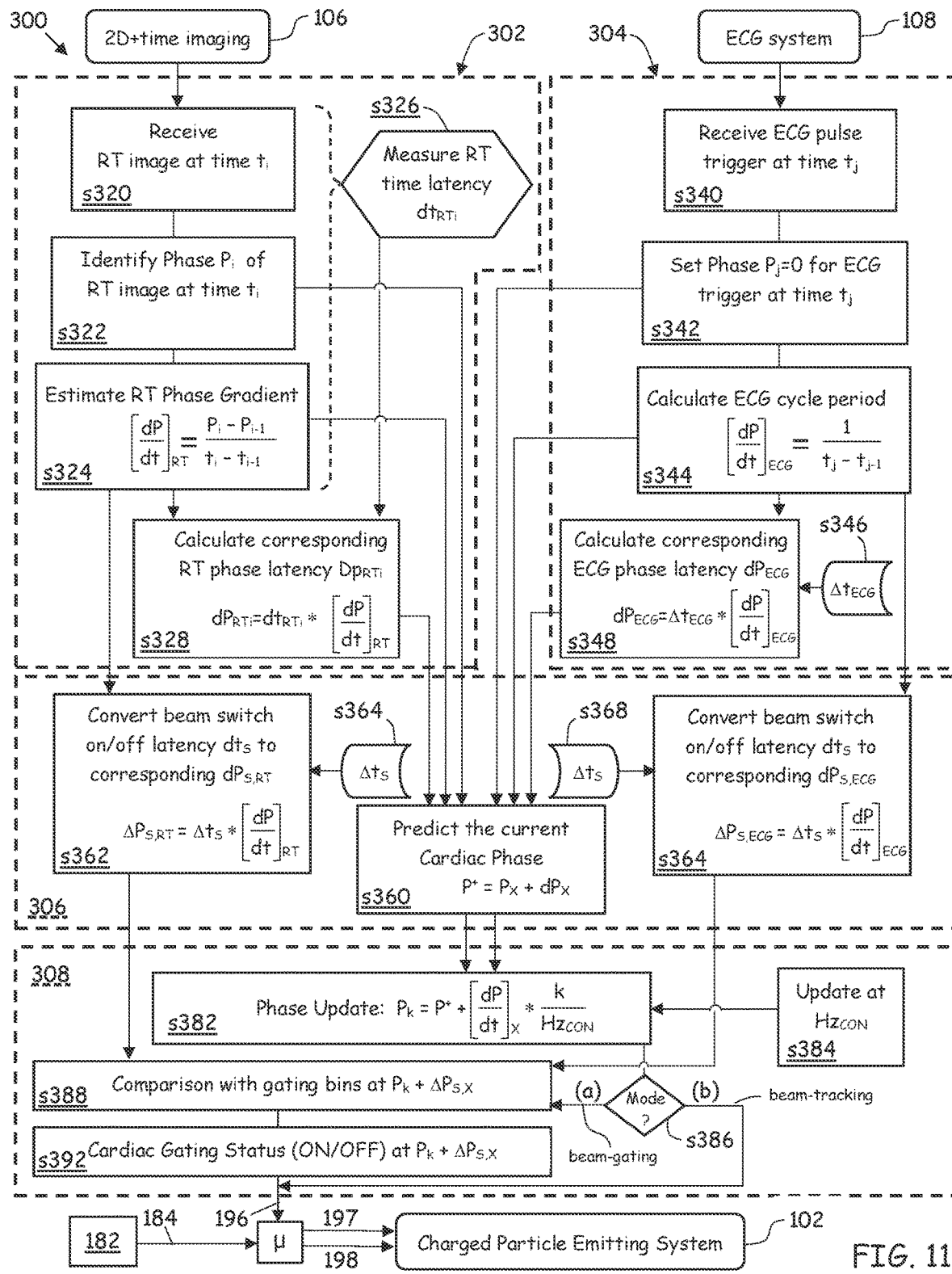
FIG. 11 is a flow chart depicting a phase prediction process according to an embodiment of the disclosure.

Referring to FIG. 11, a phase prediction process 300 embodied by the cardiac phase gating module 192 for predictively determining the gating of the charged particle emitting system 102 is depicted according to an embodiment of the disclosure. The phase prediction process 300 includes four subroutines: (1) a real-time (RT) image processing subroutine 302; (2) a heartbeat sensor processing subroutine 304; (3) a cardiac phase prediction subroutine 306; and (4) a cardiac phase update subroutine 308.

The real-time image processing subroutine 302 monitors, receives, and processes real-time images 142 from the real-time imaging system 106. The steps include receiving the real-time image 142 taken at a marked time $t_i$ (s320), identifying the cardiac phase $P_i$ corresponding to the received real-time image 142 (s322), and estimating the cardiac phase gradient $(dP/dt)_{RT}$ from the real-time information (s324), given by $$\left[\frac{dP}{dt}\right]_{RT} = \frac{P_i - P_{i-1}}{t - t_{i-1}} \qquad \text{Eq. (1)}$$

where $P_{i-1}$ is the cardiac phase of the immediately preceding cardiac phase determination from the real-time image information at time $t_{i-1}$. In some embodiments, the real-time image processing subroutine 302 measures the time required to perform steps s320 through s324, referred to as the real-time imaging time latency $dt_{RTi}$ (s326).

Having determined the cardiac phase gradient $(dP/dt)_{RT}$ and the real-time imaging time latency $dt_{RTi}$ from the real-time images, the real-time image processing subroutine 302 calculates the cardiac phase latency $dP_{RTi}$ corresponding to real-time imaging time latency $dt^{RTi}$ (s328), given by $$dP_{RTi} = dt_{RTi} * \left[\frac{dP}{dt}\right]_{RT} \qquad \text{Eq. (2)}$$

The real-time image processing subroutine 302 passes the cardiac phase $P_i$, the cardiac phase gradient $(dP/dt)_{RT}$ and the cardiac phase latency $dP_{RTi}$ of the image acquisition and processing to the cardiac phase prediction subroutine 306 and returns to step s320 to wait for further input from the real-time imaging system 106.

Meanwhile or alternatively, the heartbeat sensor processing subroutine 304 monitors, receives, and processes cardiac cycle data 174 from the heartbeat sensing system 172. For FIG. 11, as well as the figures generally, reference is made to the ECG, which is understood to be a non-limiting example of a heartbeat sensing system 172. That is, the heartbeat sensor processing subroutine 304 is representative of any calculation routine that is triggered by a characteristic of the cardiac cycle data 174 (e.g., as with the R-wave peaks of the ECG), but is not limited to an ECG. The steps of the heartbeat sensor processing subroutine 304 include receiving the trigger pulse 264 taken at a marked time $t_j$ (s340), calculating the cardiac phase gradient $(dP/dt)_{ECG}$ (s344), and estimating the corresponding cardiac phase latency $dP_ECG$ (s346) from the cardiac cycle data 174. In some embodiments, such as for an ECG, the heartbeat sensing system 172 delivers only one trigger pulse per cardiac cycle 256. For ECG systems, the trigger pulse is generated at the R-peak of the ECG signal or may correspond to a QRS complex of the cardiac electrical signal. Herein, the R-peak is designated as the beginning of the cardiac cycle 256. Unlike the real-time image processing subroutine 302, there is no need to determine the corresponding phase at the time $t_{j-1}$ of the previous trigger for the heartbeat sensor processing subroutine 304; that is, the phase lapse between times $t_j$ and $t_{j-1}$ is, by definition, 1.0. Accordingly, for such embodiments, the cardiac phase $P_j$ is set at zero (s342) and the heartbeat sensor phase gradient $(dP/dt)_{ECG}$ reduces to the inverse of the cycle period (s344) given by $$\left[\frac{dP}{dt}\right]_{ECG} = \frac{1}{t_j - t_{j-1}} \qquad \text{Eq. (3)}$$

Also, for certain heartbeat sensing systems 172 (again, such as an ECG), a heartbeat sensor time latency $\Delta t_{ECG}$ for receiving the pulse trigger (s340), setting the cardiac phase $P_3$ to zero (s342), and calculating the period (s344) is repeatable to within a small uncertainty. As such, unlike the acquisition of the real-time imaging time latency $dt_{RTi}$ for the real-time image processing subroutine 302, there is no need to measure and transfer the heartbeat sensor time latency $\Delta t_{ECG}$ within the heartbeat sensor processing subroutine 304; rather, the heartbeat sensor time latency $\Delta t_{ECG}$ may be determined a priori and entered as a fixed variable (s346) that is accessed. Knowing the heartbeat sensor time latency $\Delta t_{ECG}$ a priori, the corresponding cardiac phase latency $dP_{ECG}$ (s348) is given by $$dP_{ECG} = \Delta t_{ECG} * \left[\frac{dP}{dt}\right]_{ECG} \qquad \text{Eq. (4)}$$

The heartbeat sensor processing subroutine 304 passes the cardiac phase $P_j$, the cardiac phase gradient $(dP/dt)_{ECG}$, and the cardiac phase latency $dP_{ECG}$ to the cardiac phase prediction subroutine 306, and returns to step s340 to wait for further input from the heartbeat sensing system 172.

The cardiac phase prediction subroutine 306 receives input from the real-time image or heartbeat sensor processing subroutines 302 and 304, and predicts the current cardiac phase $P^+$ (s360) as follows:

$$P^+ = P_X + dP_X \qquad \text{Eq. (5)}$$

where $P_X$ is the most recent cardiac phase $P_i$ or $P_j$ and $dP_X$ is the most recent cardiac phase latency $dP_{RTi}$ or $dP_{ECG}$ received by the cardiac phase prediction subroutine 306. The cardiac phase prediction subroutine 306 passes the prediction $P^+$ and the cardiac phase latency $dP_X$ on to the cardiac phase update subroutine 308.

While it may seem counterintuitive to "predict" a cardiac phase that is "current," consider that, by the time the information is processed and passed on by the processing subroutine 302 or 304, such information has occurred in the past. The cardiac phase prediction subroutine 306 accounts for the time lapse, so that the current cardiac phase is predicted based on the most recently available information before being passed on to the cardiac phase update subroutine 308. Such "predicted current" cardiac phase $P^+$ provides enhanced accuracy in the millisecond or sub-millisecond time frame in which gating of the charged particle emitting system 102 is determined.

In some embodiments, the cardiac phase prediction subroutine 306 also converts a switch on/off time latency $\Delta t_S$ of the on/off switch 199 of the beam controller 116 to a corresponding switch on/off phase latency $\Delta P_{S,RT}$ or $\Delta P_{S,ECG}$ (s362 or s364). The switch on/off phase latencies $\Delta P_{S,RT}$ or $\Delta P_{S,ECG}$ are given by $$\Delta P_{S,RT} = \Delta t_S * \left[\frac{dP}{dt}\right]_{RT} \qquad \text{Eq. (6)}$$

and $$\Delta P_{S,ECG} = \Delta t_S * \left[\frac{dP}{dt}\right]_{ECG} \qquad \text{Eq. (7)}$$

where $\Delta t_S$ is the switch on/off time latency for the charged particle emitting system 102. The switch on/off time latency $\Delta t_S$ may also account for differences in the switch on latency versus the switch off latency. The switch on/off time latency $\Delta t_S$ is repeatable to within a small uncertainty and specific to a given irradiation system. Accordingly, $\Delta t_S$ may be determined a priori and entered as a fixed variable (s366 and s368). In the case of beam-tracking, the same calculation holds although $\Delta t_S$ represents the time required to load the beam parameters.

The cardiac phase update subroutine 308 receives the predicted current cardiac phase $P^+$ and the most recently calculated cardiac phase gradient $dP_X$ from the cardiac phase prediction subroutine 306. In some embodiments, the cardiac phase update subroutine 308 also receives an updated switch on/off phase latency $\Delta P_{S,X}$, which is the most recent switch on/off phase latency $\Delta P_{S,RT}$ or $\Delta P_{S,ECG}$ received from the respective processing subroutines 302 or 304.

At a phase update step s382, the cardiac phase update subroutine 308 takes the predicted current cardiac phase $P^+$ and calculates an updated cardiac phase $P_k$ as follows:

$$P_k = P^+ + \left[\frac{dP}{dt}\right]_X \left(\frac{k}{Hz_{CON}}\right) \qquad \text{Eq. (8)}$$

where $(dP/dt)_X$ is the most recent cardiac phase gradient $(dP/dt)_{RT}$ or $(dP/dt)_{ECG}$ provided by the processing subroutines 302 and 304, and k is the number of update cycles since the cardiac phase update subroutine 308 last received the predicted cardiac phase P⁺ from the cardiac phase prediction subroutine 306. The updated cardiac phase $P_k$ is an extrapolation that predicts the cardiac phase at the end of a given update cycle k (i.e., at the output of step s392) by going forward in time from the last predicted current cardiac phase P⁺. The extrapolation may be linear and is made for every update cycle k until a new predicted current cardiac phase P⁺ is received from the cardiac phase prediction subroutine 306. Upon receiving the new predicted current cardiac phase P⁺, the update cycle k is reset to zero.

The phase update (s382) is continually recalculated using the most recent current cardiac phase P⁺ and the most recent cardiac phase gradient $(dP/dt)_X$ at a steady update rate of $Hz_{CON}$ (s384), for example, at the cycle rate of a programmable logic controller (PLC) that is part of the central target motion controller 162.

In the beam-gating mode (s386(a)), the updated phase $P_k$ is compared with a prescribed phase vs. beam-gating schedule (s388), and a cardiac gating status update (s392) is sent to the processor µ of the central target motion controller 162 as the cardiac motion signal 196. The cardiac gating status may be determined by comparing the cardiac phase bins 254 to the cardiac phase $P_k + \Delta P_{S,X}$ (s388). In some embodiments, the cardiac phase prediction subroutine 306 accounts for the switch on/off time latency $\Delta t_S$ by adding the updated switch on/off phase latency $\Delta P_{S,X}$ to the updated cardiac phase $P_k$. That is, the cardiac gating status may be determined for the cardiac phase at $P_k + \Delta P_{S,X}$ (s392). In this way, the cardiac phase update subroutine 308 determines the updated cardiac phase $P_k$ at the completion of the on/off switching.

In some embodiments, the processor µ also receives the respiratory motion signal 184 from the respiratory control module 182 during beam-gating mode operation. As described above, the processor µ of the central target motion controller 162 processes the cardiac signal 196 (i.e., the cardiac gating status) and respiratory phase signal 184 and, if both are determined to be within designated treatment bins of the treatment plan 186, the gating signal 197 sent by the processor µ instructs the beam controller 116 to set the on/off switch 199 to enable the charged particle emitting system 102. If one or both of the respiratory and cardiac signals 184 and 196 are determined to be outside the designated treatment bins of the treatment plan 186, the gating signal 197 sent by the processor µ instructs the beam controller 116 to set the on/off switch 199 to gate (disable) the charged particle emitting system 102.

In the beam-tracking mode (s386(b)), the updated cardiac phase $P_k$ is passed on to the processor µ of the central target motion controller 162 as the cardiac motion signal 196. The processor µ may also receive the respiratory motion signal 184 from the respiratory control module 182. As described attendant to FIG. 5, the processor µ processes the respiratory and cardiac phase signals 184 and 196 and relays information via the digital communication signal 198 for utilization by the charged particle emitting system 102 to configure the properties of the particle beam 118.

The allocation of tasks performed within each of the subroutines 302, 304, 306, and 308 as presented is non-limiting. Various of the subroutines 302, 304, 306, and 308 may be grouped together, or divided into more subroutines. The tasks within each subroutine may also be allocated to other subroutines. For example, the switch on/off latency conversions at steps s362 and s364 may be performed within the processing subroutines 302 and 304, or within the cardiac phase update subroutine 308, or be allocated in a separate subroutine.

In operation, the real-time imaging and heartbeat sensor processing subroutines 302 and 304 may operate at non-uniform time intervals that depend on the availability of the data incoming from the real-time imaging system 106 and the heartbeat sensing system 172. The cardiac phase prediction subroutine 306 may be continuously performed at uniform time intervals governed by the cycling rate of the central target motion controller 162, utilizing the most recent predicted cardiac phase P⁺ available. The cardiac phase update subroutine 308 may be executed by a deterministic computing platform, such as real-time LINUX®. In some embodiments, the target motion controller is a programmable logic controller (PLC) with fast cycle times (e.g., within a range of 1 microsecond to 1 second). Accordingly, the cardiac phase update subroutine 308 blends the randomly acquired and calculated data from the real-time imaging and heartbeat sensor processing subroutines 302 and 304 with the uniformly cycled or lock step continuous update routine.

Functionally, cardiac phase gating module 192 includes the flexibility of allowing the usage of one or a plurality of sources of information (e.g., ECG, ultrasound) for cardiac phase identification. The ECG, for example, is only able to deliver one cardiac phase reference point per cardiac cycle (when a R-wave peak is detected), whereas the real-time images can deliver multiple cardiac phases at various time intervals during the cardiac cycle. The multiple delivery and calculation of real-time image data during a given cardiac cycle enables the real-time image data to be utilized as a time marker.

Figure 12:
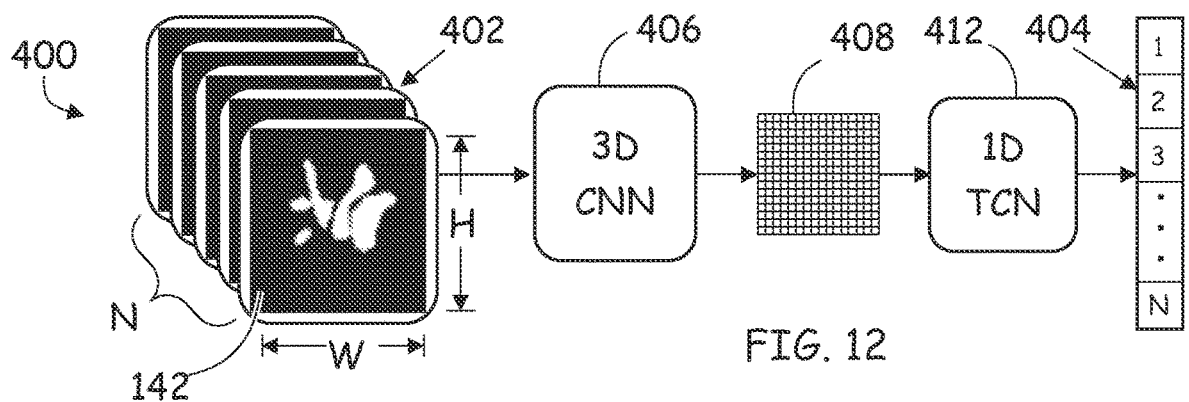
FIG. 12 is a block diagram depicting a neural network for determining the cardiac phase according to an embodiment of the disclosure.

Referring to FIG. 12, a neural network 400 for determining the cardiac phase 251 is depicted according to an embodiment of the disclosure. The neural network 400 accepts as input an image sequence 402 and outputs a phase calculation layer 404 that contains a feature corresponding to the cardiac phase value $P_i$ for each real-time image 142 in the image sequence 402.

The image sequence 402 is a plurality of the real-time images 142 (e.g., a video). The plurality of images 142 are received in the order of acquisition and may be internally buffered within the neural network 400. In some embodiments, the real-time images 142 are two-dimensional B-mode ultrasonic frames with a gray value range of 8 bits (between 0 and 255 inclusive) that are normalized between 0 and 1. The image sequence 402 has a dimension of NxHxWx1, where N is the number of real-time images 142, each real-time image 142 being an HxW array of pixels. The image sequence 402 is processed by a three-dimensional convolutional neural network (3D CNN) 406 to output a spatial feature layer 408.

The spatial feature layer 408 is processed by a one-dimensional temporal convolutional neural network (1D TCN) 412. The temporal feature layer is dimensioned at NxNf, where Nf is the number of filters. The 1D TCN 412 outputs the phase calculation layer 404. Determination of the cardiac phase value $P_i$, is performed for each of the plurality of real-time images 142 in image sequence 402 by processing the updated image sequence 402. Typical, non-limiting examples of dimensions are Nx512 for the spatial feature layer 408 and Nx1 for the phase calculation layer 404. In some embodiments, the phase calculation layer 404 is a vector of unbounded values containing a determination of the phase corresponding to each real-time image 142 in the image sequence 402.

Figure 13:
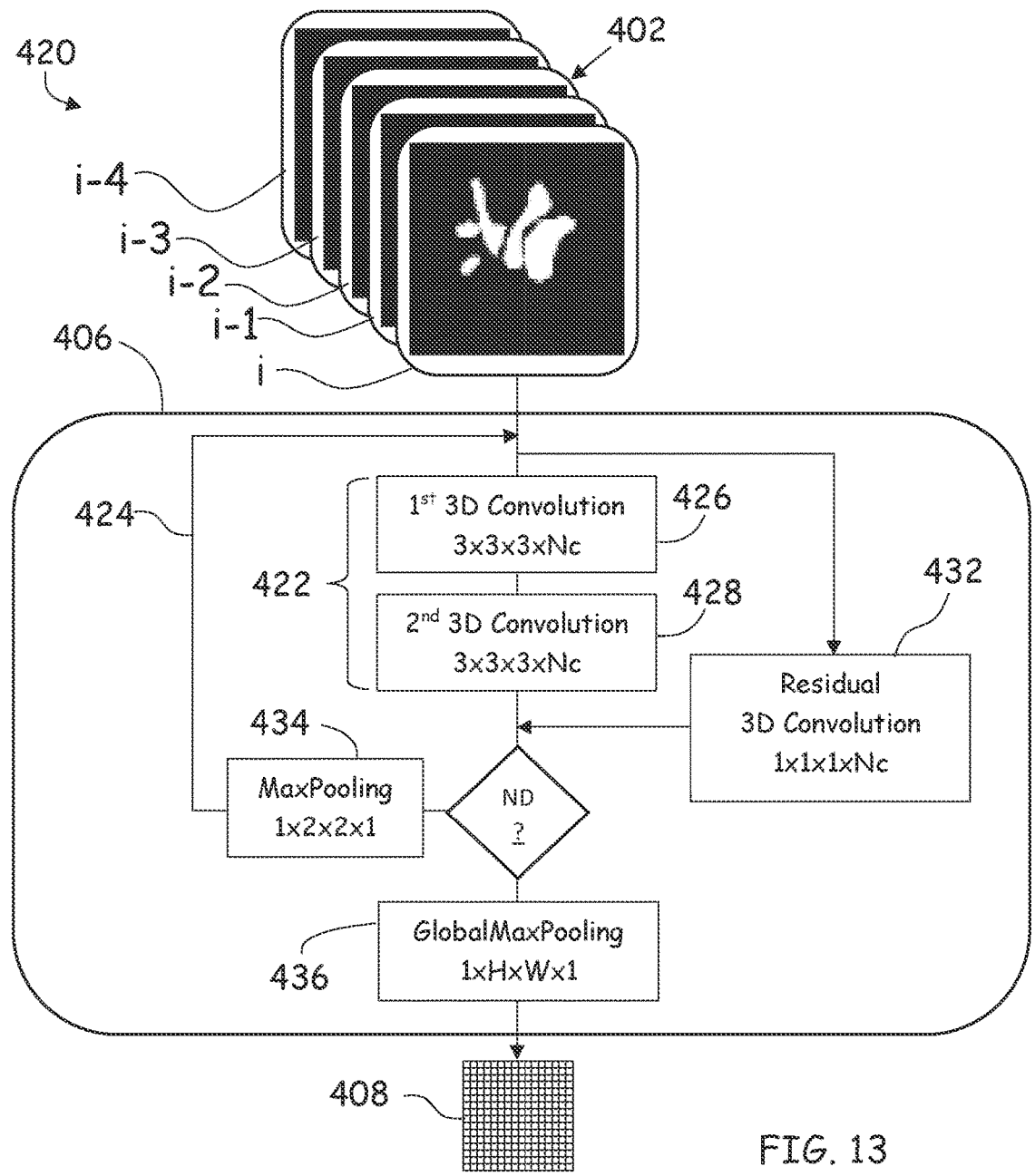
FIG. 13 is a flow chart depicting a three-dimensional convolutional neural network (3D CNN) used in the neural network of FIG. 12 according to an embodiment of the disclosure.

Referring to FIG. 13, a flow diagram 420 of the 3D CNN 406 is depicted according to an embodiment of the disclosure. The 3D CNN 406 is a multi-stage causal convolution neural network. The 3D CNN 406 includes a decomposition stage 422 that may be executed multiple times. The multiple execution is represented by a loop 424 in the flow diagram 420, which is executed a total of ND times. The decomposition stage 422 includes two consecutive 3D convolutions 426 and 428 and a residual connection 432 added after the second 3D convolution 428. Each execution of the decomposition stage 422 is followed by a maxpooling operation 434. After the last decomposition ND, the spatial dimension is reduced to one by a global maxpooling operation 436 among the height and width dimensions. In some embodiments, the 3D CNN 406 executes the decomposition stage 422 a total of six times (i.e., ND=6).

Functionally, the neural network 400 may be implemented, for example, to identify the cardiac phase value $P_i$ at step s322 of the image processing subroutine 302. The neural network 400 may also be used for phase identification during the simulation stage S201. The 3D CNN 406 extracts spatial features and short-term temporal features from the image sequence 402. The effect of each successive decomposition stage 422 and maxpooling operation 434 is to reduce the dimensionality in both height and width to reduce the resolution by a selected factor, which generates feature maps of different spatial resolution. In the depicted embodiment, as a non-limiting example, the height and width are both reduced by a factor of two, so that the resolution is reduced by four. The number of feature maps doubles with each execution of the decomposition each stage 422.

Further details regarding multi-stage causal convolution neural networks are available at Fiorito et al., "Detection of Cardiac Events in Echocardiography using 3D Convolutional Recurrent Neural Networks," *Ultrasonics Symposium (IUS), 2018 IEEE International,* 2018, and at Bai et al., "An empirical evaluation of generic convolutional and recurrent networks for sequence modeling," arXiv Prepr. arXiv1803.01271, 2018, the disclosures of which are hereby incorporated by reference herein in their entirety.

Figures 14, 15:
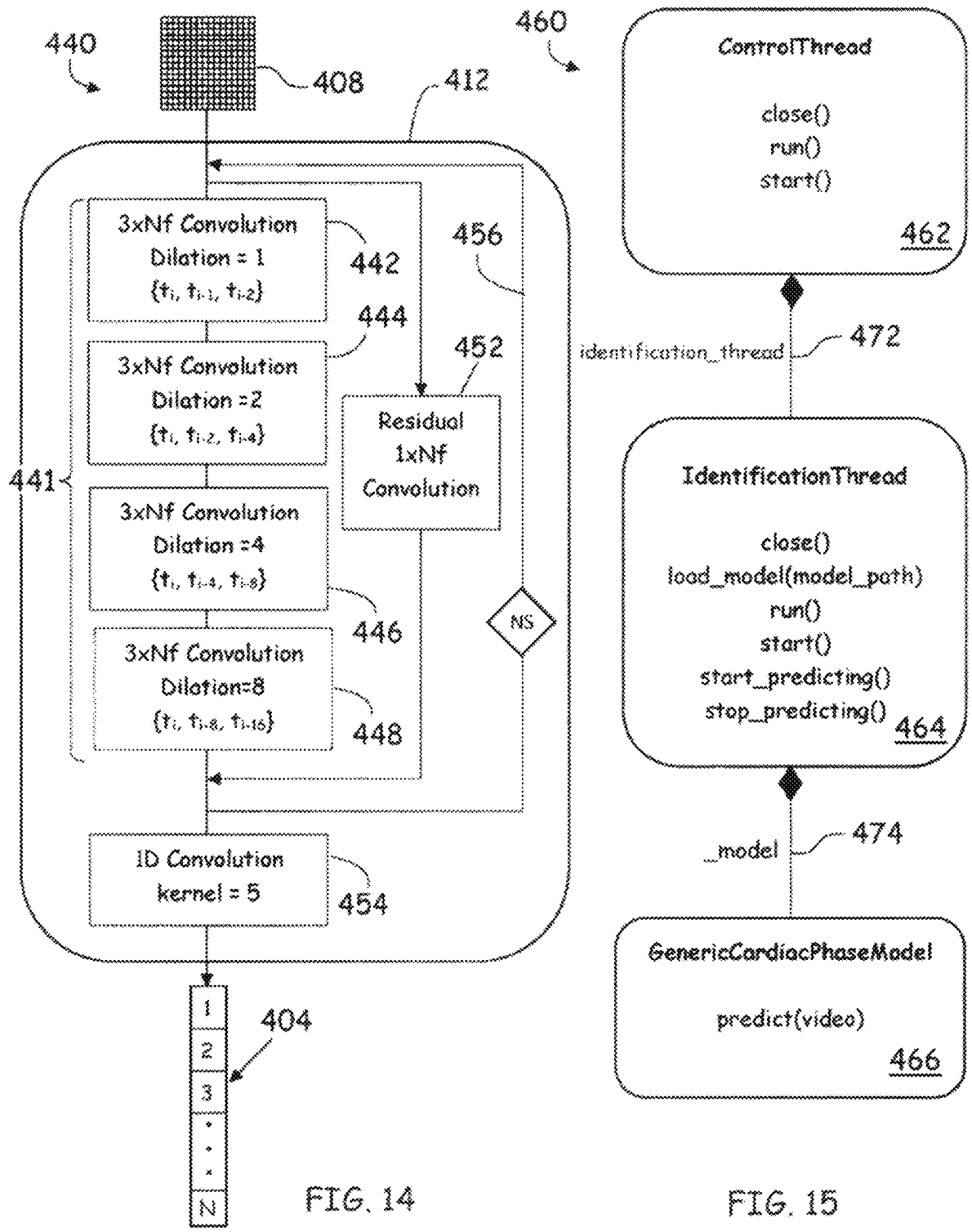
FIG. 14 is a flow chart depicting a one-dimensional temporal convolutional neural network (1D TCN) used in the neural network of FIG. 12 according to an embodiment of the disclosure.
FIG. 15 is a workflow and interface diagram of the neural network of FIG. 12 according to an embodiment of the disclosure.

Referring to FIG. 14, a flow diagram 440 of the 1D TCN 412 is depicted according to an embodiment of the disclosure. The 1D TCN 412 executes a series 441 of four consecutive dilated 1D causal convolutional layers 442, 444, 446, and 448 and a residual connection 452 added to the output of each series 441. A dilation rate of the convolution is multiplied by two for each successive convolutional layer 442 through 448. In some embodiments, a kernel size of three is used for each of the convolutional layers 442 through 448. Accordingly, the first convolutional layer 442 processes the rows of the spatial feature layer 408 corresponding to the real-time images 142 of the image sequence 402 acquired at marked time $t_i$, $t_{i-i}$, and $t_{i-2}$. The subscript qualifiers i, i−1, i−2, and so on are depicted at FIG. 13, where i corresponds to the most recently acquired real-time image 142 and the subtracted integer refers to the preceding image number relative thereto. The value of the second convolutional layer 444 processes the rows of the temporal feature layer 408 corresponding to the real-time images 142 of the image sequence 402 acquired at marked times $t_i$, $t_{i-2}$, and $t_{i-4}$; the third convolutional layer 446 processes the rows of the temporal feature layer 408 corresponding to the real-time images 142 of the image sequence 402 acquired at time $t_i$, $t_{i-4}$, and $t_{i-8}$; and the fourth convolutional layer 448 processes the rows of the temporal feature layer 408 corresponding to the real-time images 142 of the image sequence 402 acquired at time $t_i$, $t_{i-8}$, and $t_{i-16}$.

The series 441 is executed in a series loop 456 a total of NS times. Upon completion of the series loop 456, a causal 1D convolutional layer 454 with a kernel size of 5 may be used to output the phase calculation layer 404 having a single feature associated with each real-time image 142 of the image sequence 402.

Functionally, the 1D TCN 412 extracts long-term temporal features from the image sequence 402. Increasing the dilation rate for each successive convolution layer 442-448 has the effect of looking back in time over the image sequence 402 while favoring (weighting) the more recent real-time images 142. In some embodiments, the number of features at the input is 512, and the series loop 456 is executed a total of four times (NS=4), which leads to 64 features at the output. For each successive series of convolutional layers 442-448 and residual connection 452, the number of temporal features is divided by 2. In some embodiments, the phase calculation layer 404 output by the 1D TCN 412 is a vector of unbounded float values, wherein each feature of the vector corresponds to the cardiac phase determination for the associated real-time image 142.

Further details regarding one-dimensional temporal convolutional neural networks is available at Bai et al., "An empirical evaluation of generic convolutional and recurrent networks for sequence modeling," arXiv Prepr. arXiv1803.01271, 2018, the disclosure of which is incorporated by reference above.

In one embodiment, the neural network 400 is trained for multiple epochs. A 4-fold cross-validation strategy may be implemented to assess network performances. In the 4-fold approach, 75% of samples (data from patients) are used as a training set and 25% of the samples (patients) as a validation set. In some embodiments, every sample is used only once in the validation set. The model having the best correlation is selected for is selected as the motion model.

For purposes of training, the neural network 400 is easier to train when the phase of every real-time image 142 of the image sequence 402 is determined as a causal progression instead of focusing on just the most recent real-time image 142. In some embodiments, only the cardiac phase value Pi of the latest real-time image 142 of the image sequence 402 is used for further processing.

Example implementations of the neural network 400 include PYTHON® 3 with the KERAS framework using TENSORFLOW® as a backend. The neural network 400 may be trained, for example, with an ADAMAX optimizer for multiple epochs. Details about the ADAMAX optimizer can be found, for example, at Kingma et al., "Adam: A method for stochastic optimization," 3rd International Conference on Learning Representations, ICLR 2015—Conference Track Proceedings, 2015, pp. 1-15, the disclosure of which is hereby incorporated by reference herein in its entirety.

Referring to FIG. 15, a flow chart 460 depicting the workflow and interfaces of the non-invasive cardiac ablation system 100 is depicted according to an embodiment of the disclosure. The flow chart 460 is an approximation of the Unified Modeling Language (UML) convention. Each block 462, 464, and 466 of the flow chart 460 represents a class, with the block title in bold providing the class name and the list below each title providing the class methods. The links 472 and 474 extending downward from blocks 462 and 464, respectively, indicates that these classes use the linked class as an attribute. Specifically, the ControlThread class 462 has a identification thread attribute 472 which is a IdentificationThread class instance, and the IdentificationThread class 464 has a model attribute 474 which is a GenericCardiacPhaseModel class instance.

The workflow of flow chart 460 is as follows:
1) A ControlThread 462 is created, which handles the ControlRequest and ControlResponse messages.
2) The ControlThread creates a IdentificationThread 464 that handles the IdentificationRequest and PredictionResponse messages.
3) The IdentificationThread 464 instantiates a GenericCardiacPhaseModel 466 to off-load the identification requests to a graphics processing unit (GPU).
4) The ControlThread 462 receives START/STOP/CONFIGURE commands and changes the state of the IdentificationThread 464 accordingly.
5) The IdentificationThread 464 receives IdentificationRequest messages. It pre-processes the ultrasound images (resizing and rescaling) contained in the messages and handles a video buffer. It off-loads the identification to the GPU through the GenericCardiacPhaseModel 466.
6) A cardiac phase prediction is performed by the GenericCardiacPhaseModel and is given to the_IdentificationThread. The IdentificationThread sends the PredictionResponse with the predicted cardiac phase.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure. In another example, certain figures and attendant descriptions are presented as a "workflow" or a "flow chart." The sequence of the associated steps outlined therein is generally non-limiting. That is, the person of skill in the art will recognize that the sequence of the workflow may, in some instances, be changed, supplemented, or further divided without detriment.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no patent claims included in the documents are incorporated by reference herein. Any incorporation by reference of documents above is yet further limited such that any definitions provided in the documents are not incorporated by reference herein unless expressly included herein.

Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. A non-invasive cardiac ablation system, comprising:
   a real-time imaging system configured to acquire one or more cardiac images during a cardiac cycle, each cardiac image of said one or more cardiac images being acquired at time intervals;
   a target motion management system configured to update a radiation source of a therapy system; and
   a heartbeat sensor configured to acquire at least one cardiac phase reference point per cardiac cycle, said target motion management system configured to determine a predicted current cardiac phase based on a time latency between acquisition of a cardiac image of said one or more cardiac images and said cardiac phase reference point,
   wherein said real-time imaging system and said target motion management system are configured to operate simultaneously.

2. The system of claim 1, wherein each of said at least one cardiac phase reference point being acquired at non uniform time intervals, and
   wherein said target motion management system monitors said heartbeat sensor and said real-time imaging system simultaneously.

3. The system of claim 1, wherein said at least one cardiac phase reference point is an R-peak of an electrocardiogram signal.

4. The system of claim 1, wherein:
   said target motion management system is configured to determine a predicted current cardiac phase based on a time latency between acquisition of said cardiac phase reference point and a representative cardiac phase.

5. The system of claim 1, wherein said target motion management system is configured to determine a predicted cardiac phase based on a switch on/off time latency for gating an irradiation source.

6. The system of claim 5, comprising a beam controller coupled to said target motion management system for gating an irradiation source.

7. The system of claim 1, wherein said target motion management system is configured to determine a predicted cardiac phase based on a time latency for configuring a radiation beam of a radiation emitting system.

8. The system of claim 7, comprising a beam controller coupled to said target motion management system for configuring a radiation beam of an irradiation source.

9. The system of claim 6, comprising an irradiation source coupled to said beam controller.

10. The system of claim 9, wherein said irradiation source is a charged particle emitter.

11. The system of claim 1, wherein said target motion management system includes a neural network.

12. The system of claim 11, wherein said neural network is configured analyze one or more of apical 4-chamber ultrasound images, apical 2-chamber ultrasound images, parasternal ultrasound images, and short-axis ultrasound images.

13. The system of claim 11, wherein said neural network is configured to identify said representative cardiac phase in real time.

14. The system of claim 1, wherein said one or more cardiac images are ultrasound images.

15. The system of claim 14, wherein said one or more ultrasound images is a single two-dimensional image.

16. The system of claim 15, wherein said one or more ultrasound images are two non-parallel two-dimensional images.

17. The system of claim 15, wherein said one or more ultrasound images is a plurality of two-dimensional images acquired sequentially.

18. The system of claim 14, wherein said ultrasound images represent time markers of said cardiac cycle.

19. The system of claim 1, comprising a respiratory motion subsystem configured to acquire a plurality of respiratory displacement data points during a respiratory cycle.

20. A non-invasive cardiac ablation system, comprising:
a target motion management system configured to update a radiation source of a therapy system; and
a heartbeat sensor configured to acquire at least one cardiac phase reference point per cardiac cycle, said target motion management system configured to determine a predicted current cardiac phase based on a switch on/off time latency for gating an irradiation source,
wherein said target motion management system and said heartbeat sensor are configured to operate simultaneously.

21. The system of claim 20, wherein said at least one cardiac phase reference point is an R-peak of an electrocardiogram signal.

22. The system of claim 20, wherein said target motion management system is configured to determine a predicted cardiac phase based on a time latency for configuring a radiation beam of a radiation emitting system.

23. The system of claim 20, comprising a beam controller coupled to said target motion management system for gating an irradiation source.

24. The system of claim 20, wherein said target motion management system is configured to determine said predicted current cardiac phase based on a time latency for configuring a radiation beam of a radiation emitting system.

25. The system of claim 20, comprising a beam controller coupled to said target motion management system for configuring a radiation beam of an irradiation source.

26. The system of claim 25, comprising an irradiation source coupled to said beam controller.

27. The system of claim 26, wherein said irradiation source is a charged particle emitter.

28. The system of claim 20, wherein said target motion management system includes a neural network.

29. The system of claim 20, comprising a real-time imaging system configured to acquire one or more cardiac images during a cardiac cycle.

30. The system of claim 29, wherein said one or more cardiac images are ultrasound images.

31. The system of claim 30, wherein said ultrasound images represent time markers of said cardiac cycle.

32. The system of claim 20, comprising a respiratory motion subsystem configured to acquire a plurality of respiratory displacement data points during a respiratory cycle.

* * * * *